(12) United States Patent
Rehfeldt et al.

(10) Patent No.: US 11,253,182 B2
(45) Date of Patent: Feb. 22, 2022

(54) APPARATUS AND METHOD FOR POLYPHASIC MULTI-OUTPUT CONSTANT-CURRENT AND CONSTANT-VOLTAGE NEUROPHYSIOLOGICAL STIMULATION

(71) Applicant: Cadwell Laboratories, Inc., Kennewick, WA (US)

(72) Inventors: Rose Rehfeldt, Kennewick, WA (US); Ivan Amaya, Richland, WA (US); John A. Cadwell, Richland, WA (US); John A. Cadwell, Jr., Richland, WA (US)

( * ) Notice: Subject to any disclaimer, the term of this patent is extended or adjusted under 35 U.S.C. 154(b) by 91 days.

(21) Appl. No.: 16/402,456

(22) Filed: May 3, 2019

(65) Prior Publication Data

US 2019/0336019 A1 Nov. 7, 2019

Related U.S. Application Data

(60) Provisional application No. 62/667,028, filed on May 4, 2018.

(51) Int. Cl.
*A61N 1/36* (2006.01)
*A61B 5/24* (2021.01)
(Continued)

(52) U.S. Cl.
CPC ............ *A61B 5/24* (2021.01); *A61N 1/36017* (2013.01); *A61B 5/389* (2021.01); *A61B 5/4893* (2013.01); *A61B 2505/05* (2013.01)

(58) Field of Classification Search
None
See application file for complete search history.

(56) References Cited

U.S. PATENT DOCUMENTS

| 751,475 A | 2/1904 | Vilbiss |
| 972,983 A | 10/1910 | Arthur |

(Continued)

FOREIGN PATENT DOCUMENTS

| AT | 466451 T | 5/2010 |
| AT | 539680 T | 1/2012 |

(Continued)

OTHER PUBLICATIONS

Cadwell et al. "Electrophysiologic Equipment and Electrical Safety" Chapter 2, Electrodiagnosis in Clinical Neurology, Fourth Edition; Churchill Livingstone, p. 15, 30-31; 1999.

(Continued)

*Primary Examiner* — Allen Porter
*Assistant Examiner* — Skylar Lindsey Christianson
(74) *Attorney, Agent, or Firm* — Novel IP

(57) ABSTRACT

The present specification discloses an intraoperative neurophysiological monitoring (IONM) system including a computing device capable of executing an IONM software engine, a stimulation module having multiple ports and various stimulation components and recording electrodes. The system is used to implement transcranial electrical stimulation and motor evoked potential monitoring by positioning at least one recording electrode on a patient, connecting the stimulation components to at least one port on the stimulation module, positioning the stimulation components on a patient's head, activating, using the IONM software engine, at least one port, delivering stimulation to the patient; and recording a stimulatory response on the patient.

26 Claims, 12 Drawing Sheets

(51) Int. Cl.
  *A61B 5/00* (2006.01)
  *A61B 5/389* (2021.01)

(56) References Cited

U.S. PATENT DOCUMENTS

| | | |
|---|---|---|
| 1,328,624 A | 1/1920 | Graham |
| 1,477,527 A | 12/1923 | Raettig |
| 1,548,184 A | 8/1925 | Cameron |
| 1,717,480 A | 6/1929 | Wappler |
| 1,842,323 A | 1/1932 | Gluzek |
| 2,110,735 A | 3/1938 | Marton |
| 2,320,709 A | 6/1943 | Arnesen |
| 2,516,882 A | 8/1950 | Kalom |
| 2,704,064 A | 3/1955 | Fizzell |
| 2,736,002 A | 2/1956 | Oriel |
| 2,807,259 A | 9/1957 | Federico |
| 2,808,826 A | 10/1957 | Reiner |
| 2,994,324 A | 8/1961 | Lemos |
| 3,035,580 A | 5/1962 | Guiorguiev |
| 3,057,356 A | 10/1962 | Greatbatch |
| 3,060,923 A | 10/1962 | Reiner |
| 3,087,486 A | 4/1963 | Kilpatrick |
| 3,147,750 A | 9/1964 | Fry |
| 3,188,605 A | 6/1965 | Slenker |
| 3,212,496 A | 10/1965 | Preston |
| 3,219,029 A | 11/1965 | Richards |
| 3,313,293 A | 4/1967 | Chesebrough |
| 3,364,929 A | 1/1968 | Ide |
| 3,580,242 A | 5/1971 | La Croix |
| 3,611,262 A | 10/1971 | Marley |
| 3,617,616 A | 11/1971 | O'Loughlin |
| 3,641,993 A | 2/1972 | Gaarder |
| 3,646,500 A | 2/1972 | Wessely |
| 3,651,812 A | 3/1972 | Samuels |
| 3,662,744 A | 5/1972 | Richardson |
| 3,664,329 A | 5/1972 | Naylor |
| 3,682,162 A | 8/1972 | Colyer |
| 3,703,900 A | 11/1972 | Holznagel |
| 3,718,132 A | 2/1973 | Holt |
| 3,733,574 A | 5/1973 | Scoville |
| 3,785,368 A | 1/1974 | McCarthy |
| 3,830,226 A | 8/1974 | Staub |
| 3,857,398 A | 12/1974 | Rubin |
| 3,880,144 A | 4/1975 | Coursin |
| 3,933,157 A | 1/1976 | Bjurwill |
| 3,957,036 A | 5/1976 | Normann |
| 3,960,141 A | 6/1976 | Bolduc |
| 3,985,125 A | 10/1976 | Rose |
| 4,062,365 A * | 12/1977 | Kameny ............ A61N 1/36021 607/72 |
| 4,088,141 A | 5/1978 | Niemi |
| 4,099,519 A | 7/1978 | Warren |
| 4,127,312 A | 11/1978 | Fleischhacker |
| 4,141,365 A | 2/1979 | Fischell |
| 4,155,353 A | 5/1979 | Rea |
| 4,164,214 A | 8/1979 | Pelzner |
| 4,175,551 A | 11/1979 | D Haenens |
| 4,177,799 A | 12/1979 | Masreliez |
| 4,184,492 A | 1/1980 | Fastenmeier |
| 4,200,104 A | 4/1980 | Harris |
| 4,204,545 A | 5/1980 | Yamakoshi |
| 4,207,897 A | 6/1980 | Evatt |
| 4,224,949 A | 9/1980 | Scott |
| 4,226,228 A | 10/1980 | Shin |
| 4,232,680 A | 11/1980 | Hudleson |
| 4,233,987 A | 11/1980 | Feingold |
| 4,235,242 A | 11/1980 | Heule |
| 4,263,899 A | 4/1981 | Burgin |
| 4,265,237 A | 5/1981 | Schwanbom |
| 4,285,347 A | 8/1981 | Hess |
| 4,291,705 A | 9/1981 | Severinghaus |
| 4,294,245 A | 10/1981 | Bussey |
| 4,295,703 A | 10/1981 | Osborne |
| 4,299,230 A | 11/1981 | Kubota |
| 4,308,012 A | 12/1981 | Tamler |
| 4,331,157 A | 5/1982 | Keller, Jr. |
| 4,372,319 A | 2/1983 | Ichinomiya |
| 4,373,531 A | 2/1983 | Wittkampf |
| 4,374,517 A | 2/1983 | Hagiwara |
| 4,402,323 A | 9/1983 | White |
| 4,444,187 A | 4/1984 | Perlin |
| 4,461,300 A | 7/1984 | Christensen |
| 4,469,098 A | 9/1984 | Davi |
| 4,483,338 A | 11/1984 | Bloom |
| 4,485,823 A | 12/1984 | Yamaguchi |
| 4,487,489 A | 12/1984 | Takamatsu |
| 4,503,842 A | 3/1985 | Takayama |
| 4,503,863 A | 3/1985 | Katims |
| 4,510,939 A | 4/1985 | Brenman |
| 4,515,168 A | 5/1985 | Chester |
| 4,517,976 A | 5/1985 | Murakoshi |
| 4,517,983 A | 5/1985 | Toyosu |
| 4,519,403 A | 5/1985 | Dickhudt |
| 4,537,198 A | 8/1985 | Corbett |
| 4,545,374 A | 10/1985 | Jacobson |
| 4,557,273 A | 12/1985 | Stoller |
| 4,558,703 A | 12/1985 | Mark |
| 4,561,445 A | 12/1985 | Berke |
| 4,562,832 A | 1/1986 | Wilder |
| 4,565,200 A | 1/1986 | Cosman |
| 4,570,640 A | 2/1986 | Barsa |
| 4,573,448 A | 3/1986 | Kambin |
| 4,573,449 A | 3/1986 | Warnke |
| 4,576,178 A | 3/1986 | Johnson |
| 4,582,063 A | 4/1986 | Mickiewicz |
| 4,592,369 A | 6/1986 | Davis |
| 4,595,018 A | 6/1986 | Rantala |
| 4,616,635 A | 10/1986 | Caspar |
| 4,616,660 A | 10/1986 | Johns |
| 4,622,973 A | 11/1986 | Agarwala |
| 4,633,889 A | 1/1987 | Talalla |
| 4,641,661 A | 2/1987 | Kalarickal |
| 4,643,507 A | 2/1987 | Coldren |
| 4,658,835 A | 4/1987 | Pohndorf |
| 4,667,676 A | 5/1987 | Guinta |
| 4,697,598 A | 10/1987 | Bernard |
| 4,697,599 A | 10/1987 | Woodley |
| 4,705,049 A | 11/1987 | John |
| 4,716,901 A | 1/1988 | Jackson |
| 4,739,772 A | 4/1988 | Hokanson |
| 4,744,371 A | 5/1988 | Harris |
| 4,759,377 A | 7/1988 | Dykstra |
| 4,763,666 A | 8/1988 | Strian |
| 4,765,311 A | 8/1988 | Kulik |
| 4,784,150 A | 11/1988 | Voorhies |
| 4,785,812 A | 11/1988 | Pihl |
| 4,795,998 A | 1/1989 | Dunbar |
| 4,807,642 A | 2/1989 | Brown |
| 4,807,643 A | 2/1989 | Rosier |
| 4,817,587 A | 4/1989 | Janese |
| 4,817,628 A | 4/1989 | Zealear |
| 4,827,935 A | 5/1989 | Geddes |
| 4,841,973 A | 6/1989 | Stecker |
| 4,844,091 A | 7/1989 | Bellak |
| 4,862,891 A | 9/1989 | Smith |
| 4,892,105 A | 1/1990 | Prass |
| 4,895,152 A | 1/1990 | Callaghan |
| 4,920,968 A | 5/1990 | Takase |
| 4,926,865 A | 5/1990 | Oman |
| 4,926,880 A | 5/1990 | Claude |
| 4,934,377 A | 6/1990 | Bova |
| 4,934,378 A | 6/1990 | Perry, Jr. |
| 4,934,957 A | 6/1990 | Bellusci |
| 4,962,766 A | 10/1990 | Herzon |
| 4,964,411 A | 10/1990 | Johnson |
| 4,964,811 A | 10/1990 | Hayes, Sr. |
| 4,984,578 A | 1/1991 | Keppel |
| 4,998,796 A | 3/1991 | Bonanni |
| 5,007,902 A | 4/1991 | Witt |
| 5,015,247 A | 5/1991 | Michelson |
| 5,018,526 A | 5/1991 | Gaston-Johansson |
| 5,020,542 A | 6/1991 | Rossmann |
| 5,024,228 A | 6/1991 | Goldstone |
| 5,058,602 A | 10/1991 | Brody |

(56) References Cited

U.S. PATENT DOCUMENTS

| | | |
|---|---|---|
| 5,080,606 A | 1/1992 | Burkard |
| 5,081,990 A | 1/1992 | Deletis |
| 5,085,226 A | 2/1992 | DeLuca |
| 5,092,344 A | 3/1992 | Lee |
| 5,095,905 A | 3/1992 | Klepinski |
| 5,125,406 A | 6/1992 | Goldstone |
| 5,127,403 A | 7/1992 | Brownlee |
| 5,131,389 A | 7/1992 | Giordani |
| 5,143,081 A | 9/1992 | Young |
| 5,146,920 A | 9/1992 | Yuuchi |
| 5,161,533 A | 11/1992 | Prass |
| 5,163,328 A | 11/1992 | Holland |
| 5,171,279 A | 12/1992 | Mathews |
| 5,190,048 A | 3/1993 | Wilkinson |
| 5,191,896 A | 3/1993 | Gafni |
| 5,195,530 A | 3/1993 | Shindel |
| 5,195,532 A | 3/1993 | Schumacher |
| 5,196,015 A | 3/1993 | Neubardt |
| 5,199,899 A | 4/1993 | Jean |
| 5,201,325 A | 4/1993 | McEwen |
| 5,215,100 A | 6/1993 | Spitz |
| RE34,390 E | 9/1993 | Culver |
| 5,253,656 A | 10/1993 | Rincoe |
| 5,255,691 A | 10/1993 | Otten |
| 5,277,197 A | 1/1994 | Church |
| 5,282,468 A | 2/1994 | Klepinski |
| 5,284,153 A | 2/1994 | Raymond |
| 5,284,154 A | 2/1994 | Raymond |
| 5,292,309 A | 3/1994 | Van Tassel |
| 5,299,563 A | 4/1994 | Seton |
| 5,306,236 A | 4/1994 | Blumenfeld |
| 5,312,417 A | 5/1994 | Wilk |
| 5,313,956 A | 5/1994 | Knutsson |
| 5,313,962 A | 5/1994 | Obenchain |
| 5,327,902 A | 7/1994 | Lemmen |
| 5,333,618 A | 8/1994 | Lekhtman |
| 5,343,871 A | 9/1994 | Bittman |
| 5,347,989 A | 9/1994 | Monroe |
| 5,358,423 A | 10/1994 | Burkhard |
| 5,358,514 A | 10/1994 | Schulman |
| 5,368,043 A | 11/1994 | Sunouchi |
| 5,373,317 A | 12/1994 | Salvati |
| 5,375,067 A | 12/1994 | Berchin |
| 5,377,667 A | 1/1995 | Patton |
| 5,381,805 A | 1/1995 | Tuckett |
| 5,383,876 A | 1/1995 | Nardella |
| 5,389,069 A | 2/1995 | Weaver |
| 5,405,365 A | 4/1995 | Hoegnelid |
| 5,413,111 A | 5/1995 | Wilkinson |
| 5,454,365 A | 10/1995 | Bonutti |
| 5,470,349 A | 11/1995 | Kleditsch |
| 5,472,426 A | 12/1995 | Bonati |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,485,852 A | 1/1996 | Johnson |
| 5,491,299 A | 2/1996 | Naylor |
| 5,514,005 A | 5/1996 | Jaycox |
| 5,514,165 A | 5/1996 | Malaugh |
| 5,522,386 A | 6/1996 | Lerner |
| 5,540,235 A | 7/1996 | Wilson |
| 5,549,656 A | 8/1996 | Reiss |
| 5,560,372 A | 10/1996 | Cory |
| 5,565,779 A | 10/1996 | Arakawa |
| 5,566,678 A | 10/1996 | Cadwell |
| 5,569,248 A | 10/1996 | Mathews |
| 5,575,284 A | 11/1996 | Athan |
| 5,579,781 A | 12/1996 | Cooke |
| 5,591,216 A | 1/1997 | Testerman |
| 5,593,429 A | 1/1997 | Ruff |
| 5,599,279 A | 2/1997 | Slotman |
| 5,601,608 A | 2/1997 | Mouchawar |
| 5,618,208 A | 4/1997 | Crouse |
| 5,620,483 A | 4/1997 | Minogue |
| 5,622,515 A | 4/1997 | Hotea |
| 5,630,813 A | 5/1997 | Kieturakis |
| 5,634,472 A | 6/1997 | Raghuprasad |
| 5,671,752 A | 9/1997 | Sinderby |
| 5,681,265 A | 10/1997 | Maeda |
| 5,687,080 A | 11/1997 | Hoyt |
| 5,707,359 A | 1/1998 | Bufalini |
| 5,711,307 A | 1/1998 | Smits |
| 5,725,514 A | 3/1998 | Grinblat |
| 5,728,046 A | 3/1998 | Mayer |
| 5,741,253 A | 4/1998 | Michelson |
| 5,741,261 A | 4/1998 | Moskovitz |
| 5,759,159 A | 6/1998 | Masreliez |
| 5,769,781 A | 6/1998 | Chappuis |
| 5,772,597 A | 6/1998 | Goldberger |
| 5,772,661 A | 6/1998 | Michelson |
| 5,775,331 A | 7/1998 | Raymond |
| 5,776,144 A | 7/1998 | Leysieffer |
| 5,779,642 A | 7/1998 | Nightengale |
| 5,785,648 A | 7/1998 | Min |
| 5,785,658 A | 7/1998 | Benaron |
| 5,792,044 A | 8/1998 | Foley |
| 5,795,291 A | 8/1998 | Koros |
| 5,797,854 A | 8/1998 | Hedgecock |
| 5,806,522 A | 9/1998 | Katims |
| 5,814,073 A | 9/1998 | Bonutti |
| 5,830,150 A | 11/1998 | Palmer |
| 5,830,151 A | 11/1998 | Hadzic |
| 5,833,714 A | 11/1998 | Loeb |
| 5,836,880 A | 11/1998 | Pratt |
| 5,851,191 A | 12/1998 | Gozani |
| 5,853,373 A | 12/1998 | Griffith |
| 5,857,986 A | 1/1999 | Moriyasu |
| 5,860,829 A | 1/1999 | Hower |
| 5,860,973 A | 1/1999 | Michelson |
| 5,862,314 A | 1/1999 | Jeddeloh |
| 5,868,668 A | 2/1999 | Weiss |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,891,147 A | 4/1999 | Moskovitz |
| 5,895,298 A | 4/1999 | Faupel |
| 5,902,231 A | 5/1999 | Foley |
| 5,924,984 A | 7/1999 | Rao |
| 5,928,030 A | 7/1999 | Daoud |
| 5,928,139 A | 7/1999 | Koros |
| 5,928,158 A | 7/1999 | Aristides |
| 5,931,777 A | 8/1999 | Sava |
| 5,944,658 A | 8/1999 | Koros |
| 5,954,635 A | 9/1999 | Foley |
| 5,954,716 A | 9/1999 | Sharkey |
| 5,993,385 A | 11/1999 | Johnston |
| 5,993,434 A | 11/1999 | Dev |
| 6,004,262 A | 12/1999 | Putz |
| 6,004,312 A | 12/1999 | Finneran |
| 6,004,341 A | 12/1999 | Zhu |
| 6,009,347 A | 12/1999 | Hofmann |
| 6,011,985 A | 1/2000 | Athan |
| 6,027,456 A | 2/2000 | Feler |
| 6,029,090 A | 2/2000 | Herbst |
| 6,038,469 A | 3/2000 | Karlsson |
| 6,038,477 A | 3/2000 | Kayyali |
| 6,042,540 A | 3/2000 | Johnston |
| 6,050,992 A | 4/2000 | Nichols |
| 6,074,343 A | 6/2000 | Nathanson |
| 6,077,237 A | 6/2000 | Campbell t al. |
| 6,095,987 A | 8/2000 | Shmulewitz |
| 6,104,957 A | 8/2000 | Alo |
| 6,104,960 A | 8/2000 | Duysens |
| 6,119,068 A | 9/2000 | Kannonji |
| 6,120,503 A | 9/2000 | Michelson |
| 6,126,660 A | 10/2000 | Dietz |
| 6,128,576 A | 10/2000 | Nishimoto |
| 6,132,386 A | 10/2000 | Gozani |
| 6,132,387 A | 10/2000 | Gozani |
| 6,135,965 A | 10/2000 | Tumer |
| 6,139,493 A | 10/2000 | Koros |
| 6,139,545 A | 10/2000 | Utley |

(56) References Cited

U.S. PATENT DOCUMENTS

| | | |
|---|---|---|
| 6,146,334 A | 11/2000 | Kay |
| 6,146,335 A | 11/2000 | Gozani |
| 6,152,871 A | 11/2000 | Foley |
| 6,161,047 A | 12/2000 | King |
| 6,181,961 B1 | 1/2001 | Prass |
| 6,196,969 B1 | 3/2001 | Bester |
| 6,206,826 B1 | 3/2001 | Mathews |
| 6,210,324 B1 | 4/2001 | Reno |
| 6,214,035 B1 | 4/2001 | Streeter |
| 6,224,545 B1 | 5/2001 | Cocchia |
| 6,224,549 B1 | 5/2001 | Drongelen |
| 6,234,953 B1 | 5/2001 | Thomas |
| 6,249,706 B1 | 6/2001 | Sobota |
| 6,259,945 B1 | 7/2001 | Epstein |
| 6,266,558 B1 | 7/2001 | Gozani |
| 6,273,905 B1 | 8/2001 | Streeter |
| 6,287,322 B1 | 9/2001 | Zhu |
| 6,292,701 B1 | 9/2001 | Prass |
| 6,298,256 B1 | 10/2001 | Meyer |
| 6,302,842 B1 | 10/2001 | Auerbach |
| 6,306,100 B1 | 10/2001 | Prass |
| 6,309,349 B1 | 10/2001 | Bertolero |
| 6,312,392 B1 | 11/2001 | Herzon |
| 6,314,324 B1 | 11/2001 | Lattner |
| 6,325,764 B1 | 12/2001 | Griffith |
| 6,334,068 B1 | 12/2001 | Hacker |
| 6,346,078 B1 | 2/2002 | Ellman |
| 6,348,058 B1 | 2/2002 | Melkent |
| 6,366,813 B1 | 4/2002 | Dilorenzo |
| 6,391,005 B1 | 5/2002 | Lum |
| 6,393,325 B1 | 5/2002 | Mann |
| 6,425,859 B1 | 7/2002 | Foley |
| 6,425,901 B1 | 7/2002 | Zhu |
| 6,441,747 B1 | 8/2002 | Khair |
| 6,450,952 B1 | 9/2002 | Rioux |
| 6,451,015 B1 | 9/2002 | Rittman, III |
| 6,461,352 B2 | 10/2002 | Morgan |
| 6,466,817 B1 | 10/2002 | Kaula |
| 6,487,446 B1 | 11/2002 | Hill |
| 6,500,128 B2 | 12/2002 | Marino |
| 6,500,173 B2 | 12/2002 | Underwood |
| 6,500,180 B1 | 12/2002 | Foley |
| 6,500,210 B1 | 12/2002 | Sabolich |
| 6,507,755 B1 | 1/2003 | Gozani |
| 6,511,427 B1 | 1/2003 | Sliwa, Jr. |
| 6,535,759 B1 | 3/2003 | Epstein |
| 6,543,299 B2 | 4/2003 | Taylor |
| 6,546,271 B1 | 4/2003 | Reisfeld |
| 6,564,078 B1 | 5/2003 | Marino |
| 6,568,961 B1 | 5/2003 | Liburdi |
| 6,577,236 B2 | 6/2003 | Harman |
| 6,579,244 B2 | 6/2003 | Goodwin |
| 6,582,441 B1 | 6/2003 | He |
| 6,585,638 B1 | 7/2003 | Yamamoto |
| 6,609,018 B2 | 8/2003 | Cory |
| 6,618,626 B2 | 9/2003 | West, Jr. |
| 6,623,500 B1 | 9/2003 | Cook |
| 6,638,101 B1 | 10/2003 | Botelho |
| 6,712,795 B1 | 3/2004 | Cohen |
| 6,719,692 B2 | 4/2004 | Kleffner |
| 6,730,021 B2 | 5/2004 | Vassiliades, Jr. |
| 6,770,074 B2 | 8/2004 | Michelson |
| 6,805,668 B1 | 10/2004 | Cadwell |
| 6,819,956 B2 | 11/2004 | Dilorenzo |
| 6,839,594 B2 | 1/2005 | Cohen |
| 6,847,849 B2 | 1/2005 | Mamo |
| 6,851,430 B2 | 2/2005 | Tsou |
| 6,855,105 B2 | 2/2005 | Jackson, III |
| 6,870,109 B1 | 3/2005 | Villarreal |
| 6,901,928 B2 | 6/2005 | Loubser |
| 6,902,569 B2 | 6/2005 | Parmer |
| 6,916,294 B2 | 7/2005 | Ayad |
| 6,916,330 B2 | 7/2005 | Simonson |
| 6,926,728 B2 | 8/2005 | Zucherman |
| 6,929,606 B2 | 8/2005 | Ritland |
| 6,932,816 B2 | 8/2005 | Phan |
| 6,945,933 B2 | 9/2005 | Branch |
| 7,024,247 B2 | 4/2006 | Gliner |
| 7,072,521 B1 | 7/2006 | Cadwell |
| 7,079,883 B2 | 7/2006 | Marino |
| 7,089,059 B1 | 8/2006 | Pless |
| 7,104,965 B1 | 9/2006 | Jiang |
| 7,129,836 B2 | 10/2006 | Lawson |
| 7,153,279 B2 | 12/2006 | Ayad |
| 7,156,686 B1 | 1/2007 | Sekela |
| 7,177,677 B2 | 2/2007 | Kaula |
| 7,214,197 B2 | 5/2007 | Prass |
| 7,216,001 B2 | 5/2007 | Hacker |
| 7,230,688 B1 | 6/2007 | Villarreal |
| 7,236,822 B2 | 6/2007 | Dobak, III |
| 7,258,688 B1 | 8/2007 | Shah |
| 7,261,688 B2 | 8/2007 | Smith |
| 7,294,127 B2 | 11/2007 | Leung |
| 7,306,563 B2 | 12/2007 | Huang |
| 7,310,546 B2 | 12/2007 | Prass |
| 7,363,079 B1 | 4/2008 | Thacker |
| 7,374,448 B1 | 5/2008 | Jepsen |
| D574,955 S | 8/2008 | Lash |
| 7,470,236 B1 | 12/2008 | Kelleher |
| 7,496,407 B2 | 2/2009 | Odderson |
| 7,522,953 B2 | 4/2009 | Kaula |
| 7,546,993 B1 | 6/2009 | Walker |
| 7,605,738 B2 | 10/2009 | Kuramochi |
| 7,664,544 B2 | 2/2010 | Miles |
| 7,689,292 B2 | 3/2010 | Hadzic |
| 7,713,210 B2 | 5/2010 | Byrd |
| D621,041 S | 8/2010 | Mao |
| 7,775,974 B2 | 8/2010 | Buckner |
| 7,789,695 B2 | 9/2010 | Radle |
| 7,789,833 B2 | 9/2010 | Urbano |
| 7,801,601 B2 | 9/2010 | Maschino |
| 7,824,410 B2 | 11/2010 | Simonson |
| 7,869,881 B2 | 1/2011 | Libbus |
| 7,878,981 B2 | 2/2011 | Strother |
| 7,914,350 B1 | 3/2011 | Bozich |
| 7,963,927 B2 | 6/2011 | Kelleher |
| 7,974,702 B1 | 7/2011 | Fain |
| 7,983,761 B2 | 7/2011 | Giuntoli |
| 7,987,001 B2 | 7/2011 | Teichman |
| 7,988,688 B2 | 8/2011 | Webb |
| 7,993,269 B2 | 8/2011 | Donofrio |
| 8,002,770 B2 | 8/2011 | Swanson |
| 8,061,014 B2 | 11/2011 | Smith |
| 8,068,910 B2 | 11/2011 | Gerber |
| 8,126,736 B2 | 2/2012 | Anderson |
| 8,137,284 B2 | 3/2012 | Miles |
| 8,147,421 B2 | 4/2012 | Farquhar |
| 8,160,694 B2 | 4/2012 | Salmon |
| 8,192,437 B2 | 6/2012 | Simonson |
| 8,255,045 B2 | 8/2012 | Gharib |
| 8,295,933 B2 | 10/2012 | Gerber |
| D670,656 S | 11/2012 | Lee |
| 8,323,208 B2 | 12/2012 | Davis |
| 8,343,079 B2 | 1/2013 | Bartol |
| 8,374,673 B2 | 2/2013 | Adcox |
| RE44,049 E | 3/2013 | Herzon |
| 8,419,758 B2 | 4/2013 | Smith |
| 8,428,733 B2 | 4/2013 | Carlson |
| 8,457,734 B2 | 6/2013 | Libbus |
| 8,498,717 B2 | 7/2013 | Lee |
| 8,515,520 B2 | 8/2013 | Brunnett |
| 8,568,312 B2 | 10/2013 | Cusimano Reaston |
| 8,568,317 B1 | 10/2013 | Gharib |
| 8,594,779 B2 | 11/2013 | Denison |
| 8,670,830 B2 | 3/2014 | Carlson |
| 8,680,986 B2 | 3/2014 | Costantino |
| 8,688,237 B2 | 4/2014 | Stanislaus |
| 8,695,957 B2 | 4/2014 | Quintania |
| 8,740,783 B2 | 6/2014 | Gharib |
| 8,753,333 B2 | 6/2014 | Johnson |
| 8,764,654 B2 | 7/2014 | Chmiel |
| 8,805,527 B2 | 8/2014 | Mumford |
| 8,876,813 B2 | 11/2014 | Min |
| 8,886,280 B2 | 11/2014 | Kartush |

(56) References Cited

U.S. PATENT DOCUMENTS

| | | |
|---|---|---|
| 8,892,259 B2 | 11/2014 | Bartol |
| 8,926,509 B2 | 1/2015 | Magar |
| 8,942,797 B2 | 1/2015 | Bartol |
| 8,956,418 B2 | 2/2015 | Wasielewski |
| 8,958,869 B2 | 2/2015 | Kelleher |
| 8,971,983 B2 | 3/2015 | Gilmore |
| 8,986,301 B2 | 3/2015 | Wolf |
| 8,989,855 B2 | 3/2015 | Murphy |
| 9,031,658 B2 | 5/2015 | Chiao |
| 9,037,226 B2 | 5/2015 | Hacker |
| 9,078,671 B2 | 7/2015 | Beale |
| 9,084,550 B1 | 7/2015 | Bartol |
| 9,084,551 B2 | 7/2015 | Brunnett |
| 9,119,533 B2 | 9/2015 | Ghaffari |
| 9,121,423 B2 | 9/2015 | Sharpe |
| 9,149,188 B2 | 10/2015 | Eng |
| 9,155,503 B2 | 10/2015 | Cadwell |
| 9,204,830 B2 | 12/2015 | Zand |
| 9,247,952 B2 | 2/2016 | Bleich |
| 9,295,401 B2 | 3/2016 | Cadwell |
| 9,295,461 B2 | 3/2016 | Bojarski |
| 9,339,332 B2 | 5/2016 | Srivastava |
| 9,352,153 B2 | 5/2016 | Van Dijk |
| 9,370,654 B2 | 6/2016 | Scheiner |
| 9,579,503 B2 | 2/2017 | McKinney |
| 9,616,233 B2 * | 4/2017 | Shi ............... A61N 1/36128 |
| 9,622,684 B2 | 4/2017 | Wybo |
| 9,714,350 B2 | 7/2017 | Hwang |
| 9,730,634 B2 | 8/2017 | Cadwell |
| 9,820,768 B2 | 11/2017 | Gee |
| 9,855,431 B2 | 1/2018 | Ternes |
| 9,913,594 B2 | 3/2018 | Li |
| 9,935,395 B1 | 4/2018 | Jepsen |
| 9,999,719 B2 | 6/2018 | Kitchen |
| 10,022,090 B2 | 7/2018 | Whitman |
| 10,039,461 B2 | 8/2018 | Cadwell |
| 10,039,915 B2 | 8/2018 | McFarlin |
| 10,092,349 B2 | 10/2018 | Engeberg |
| 10,154,792 B2 | 12/2018 | Sakai |
| 10,292,883 B2 | 5/2019 | Lee |
| 10,342,452 B2 | 7/2019 | Sterrantino |
| 10,349,862 B2 | 7/2019 | Sterrantino |
| 10,398,369 B2 | 9/2019 | Brown |
| 10,418,750 B2 | 9/2019 | Jepsen |
| 10,631,912 B2 | 4/2020 | McFarlin |
| 2001/0031916 A1 | 10/2001 | Bennett |
| 2001/0039949 A1 | 11/2001 | Loubser |
| 2001/0049524 A1 | 12/2001 | Morgan |
| 2001/0056280 A1 | 12/2001 | Underwood |
| 2002/0001995 A1 | 1/2002 | Lin |
| 2002/0001996 A1 | 1/2002 | Seki |
| 2002/0007129 A1 | 1/2002 | Marino |
| 2002/0007188 A1 | 1/2002 | Arambula |
| 2002/0055295 A1 | 5/2002 | Toshio |
| 2002/0065481 A1 | 5/2002 | Cory |
| 2002/0072686 A1 | 6/2002 | Hoey |
| 2002/0095080 A1 | 7/2002 | Cory |
| 2002/0149384 A1 | 10/2002 | Reasoner |
| 2002/0161415 A1 | 10/2002 | Cohen |
| 2002/0183647 A1 | 12/2002 | Gozani |
| 2002/0193779 A1 | 12/2002 | Yamazaki |
| 2002/0193843 A1 | 12/2002 | Hill |
| 2002/0194934 A1 | 12/2002 | Taylor |
| 2003/0032966 A1 | 2/2003 | Foley |
| 2003/0045808 A1 | 3/2003 | Kaula |
| 2003/0078618 A1 | 4/2003 | Fey |
| 2003/0088185 A1 | 5/2003 | Prass |
| 2003/0105503 A1 | 6/2003 | Marino |
| 2003/0171747 A1 | 9/2003 | Kanehira |
| 2003/0199191 A1 | 10/2003 | Ward |
| 2003/0212335 A1 | 11/2003 | Huang |
| 2004/0019370 A1 | 1/2004 | Gliner |
| 2004/0034340 A1 | 2/2004 | Biscup |
| 2004/0068203 A1 | 4/2004 | Gellman |
| 2004/0135528 A1 | 7/2004 | Yasohara |
| 2004/0172114 A1 | 9/2004 | Hadzic |
| 2004/0199084 A1 | 10/2004 | Kelleher |
| 2004/0204628 A1 | 10/2004 | Rovegno |
| 2004/0225228 A1 | 11/2004 | Ferree |
| 2004/0229495 A1 | 11/2004 | Negishi |
| 2004/0230131 A1 | 11/2004 | Kassab |
| 2004/0260358 A1 | 12/2004 | Vaughan |
| 2005/0004593 A1 | 1/2005 | Simonson |
| 2005/0004623 A1 | 1/2005 | Miles |
| 2005/0075067 A1 | 4/2005 | Lawson |
| 2005/0075578 A1 | 4/2005 | Gharib |
| 2005/0080418 A1 | 4/2005 | Simonson |
| 2005/0085743 A1 | 4/2005 | Hacker |
| 2005/0119660 A1 | 6/2005 | Bourlion |
| 2005/0149143 A1 | 7/2005 | Libbus |
| 2005/0159659 A1 | 7/2005 | Sawan |
| 2005/0182454 A1 | 8/2005 | Gharib |
| 2005/0215993 A1 | 9/2005 | Phan |
| 2005/0256582 A1 | 11/2005 | Ferree |
| 2005/0261559 A1 | 11/2005 | Mumford |
| 2006/0004424 A1 * | 1/2006 | Loeb ............... A61N 1/3605 607/63 |
| 2006/0009754 A1 | 1/2006 | Boese |
| 2006/0025702 A1 | 2/2006 | Sterrantino |
| 2006/0025703 A1 | 2/2006 | Miles |
| 2006/0052828 A1 | 3/2006 | Kim |
| 2006/0069315 A1 | 3/2006 | Miles |
| 2006/0085048 A1 | 4/2006 | Cory |
| 2006/0085049 A1 | 4/2006 | Cory |
| 2006/0122514 A1 | 6/2006 | Byrd |
| 2006/0173383 A1 | 8/2006 | Daniel |
| 2006/0200023 A1 | 9/2006 | Melkent |
| 2006/0241725 A1 | 10/2006 | Libbus |
| 2006/0258951 A1 | 11/2006 | Bleich |
| 2006/0264777 A1 * | 11/2006 | Drew ............... A61N 1/36082 600/547 |
| 2006/0276702 A1 | 12/2006 | McGinnis |
| 2006/0292919 A1 | 12/2006 | Kruss |
| 2007/0016097 A1 | 1/2007 | Farquhar |
| 2007/0021682 A1 | 1/2007 | Gharib |
| 2007/0032841 A1 | 2/2007 | Urmey |
| 2007/0049962 A1 | 3/2007 | Marino |
| 2007/0097719 A1 * | 5/2007 | Parramon ............... A61N 1/378 363/72 |
| 2007/0184422 A1 | 8/2007 | Takahashi |
| 2007/0270918 A1 | 11/2007 | De Bel |
| 2007/0282217 A1 | 12/2007 | McGinnis |
| 2008/0015612 A1 | 1/2008 | Urmey |
| 2008/0027507 A1 | 1/2008 | Bijelic |
| 2008/0039914 A1 | 2/2008 | Cory |
| 2008/0058606 A1 | 3/2008 | Miles |
| 2008/0064976 A1 | 3/2008 | Kelleher |
| 2008/0065144 A1 | 3/2008 | Marino |
| 2008/0065178 A1 | 3/2008 | Kelleher |
| 2008/0071191 A1 | 3/2008 | Kelleher |
| 2008/0077198 A1 | 3/2008 | Webb |
| 2008/0082136 A1 | 4/2008 | Gaudiani |
| 2008/0097164 A1 | 4/2008 | Miles |
| 2008/0167574 A1 | 7/2008 | Farquhar |
| 2008/0183190 A1 | 7/2008 | Adcox |
| 2008/0183915 A1 | 7/2008 | lima |
| 2008/0194970 A1 | 8/2008 | Steers |
| 2008/0214903 A1 | 9/2008 | Orbach |
| 2008/0218393 A1 | 9/2008 | Kuramochi |
| 2008/0254672 A1 | 10/2008 | Dennes |
| 2008/0269777 A1 | 10/2008 | Appenrodt |
| 2008/0281313 A1 | 11/2008 | Fagin |
| 2008/0300650 A1 | 12/2008 | Gerber |
| 2008/0306348 A1 | 12/2008 | Kuo |
| 2009/0018399 A1 | 1/2009 | Martinelli |
| 2009/0088660 A1 | 4/2009 | McMorrow |
| 2009/0105604 A1 | 4/2009 | Bertagnoli |
| 2009/0143797 A1 | 6/2009 | Smith |
| 2009/0177112 A1 | 7/2009 | Gharib |
| 2009/0182322 A1 | 7/2009 | D Amelio |
| 2009/0197476 A1 | 8/2009 | Wallace |
| 2009/0204016 A1 | 8/2009 | Gharib |
| 2009/0209879 A1 | 8/2009 | Kaula |
| 2009/0221153 A1 | 9/2009 | Santangelo |

(56) References Cited

U.S. PATENT DOCUMENTS

| | | | |
|---|---|---|---|
| 2009/0240117 A1 | 9/2009 | Chmiel | |
| 2009/0259108 A1 | 10/2009 | Miles | |
| 2009/0279767 A1 | 11/2009 | Kukuk | |
| 2009/0281595 A1* | 11/2009 | King | A61N 1/36185 607/46 |
| 2009/0299439 A1 | 12/2009 | Mire | |
| 2010/0004949 A1* | 1/2010 | O'Brien | G16H 15/00 705/3 |
| 2010/0036280 A1 | 2/2010 | Soren | |
| 2010/0036384 A1 | 2/2010 | Gorek | |
| 2010/0049188 A1* | 2/2010 | Nelson | A61B 18/1206 606/34 |
| 2010/0106011 A1 | 4/2010 | Byrd | |
| 2010/0152604 A1 | 6/2010 | Kaula | |
| 2010/0152811 A1 | 6/2010 | Flaherty | |
| 2010/0152812 A1 | 6/2010 | Flaherty | |
| 2010/0160731 A1 | 6/2010 | Giovannini | |
| 2010/0168561 A1 | 7/2010 | Anderson | |
| 2010/0191311 A1 | 7/2010 | Scheiner | |
| 2010/0286554 A1 | 11/2010 | Davis | |
| 2010/0317989 A1 | 12/2010 | Gharib | |
| 2011/0004207 A1 | 1/2011 | Wallace | |
| 2011/0028860 A1 | 2/2011 | Chenaux | |
| 2011/0071418 A1 | 3/2011 | Stellar | |
| 2011/0082383 A1 | 4/2011 | Cory | |
| 2011/0160731 A1 | 6/2011 | Bleich | |
| 2011/0184308 A1 | 7/2011 | Kaula | |
| 2011/0230734 A1 | 9/2011 | Fain | |
| 2011/0230782 A1 | 9/2011 | Bartol | |
| 2011/0245647 A1 | 10/2011 | Stanislaus | |
| 2011/0270120 A1 | 11/2011 | McFarlin | |
| 2011/0270121 A1 | 11/2011 | Johnson | |
| 2011/0295579 A1 | 12/2011 | Tang | |
| 2011/0313530 A1 | 12/2011 | Gharib | |
| 2012/0004516 A1 | 1/2012 | Eng | |
| 2012/0071784 A1 | 3/2012 | Melkent | |
| 2012/0109000 A1 | 5/2012 | Kaula | |
| 2012/0109004 A1 | 5/2012 | Cadwell | |
| 2012/0220891 A1 | 8/2012 | Kaula | |
| 2012/0238893 A1 | 9/2012 | Farquhar | |
| 2012/0245439 A1 | 9/2012 | Andre | |
| 2012/0277780 A1 | 11/2012 | Smith | |
| 2012/0296230 A1 | 11/2012 | Davis | |
| 2013/0027186 A1* | 1/2013 | Cinbis | A61B 5/0028 340/10.1 |
| 2013/0030257 A1 | 1/2013 | Nakata | |
| 2013/0090641 A1 | 4/2013 | McKinney | |
| 2013/0245722 A1 | 9/2013 | Ternes | |
| 2013/0261422 A1 | 10/2013 | Gilmore | |
| 2013/0267874 A1 | 10/2013 | Marcotte | |
| 2014/0058284 A1 | 2/2014 | Bartol | |
| 2014/0073985 A1 | 3/2014 | Sakai | |
| 2014/0074084 A1 | 3/2014 | Engeberg | |
| 2014/0088463 A1 | 3/2014 | Wolf | |
| 2014/0121555 A1 | 5/2014 | Scott | |
| 2014/0275914 A1 | 9/2014 | Li | |
| 2014/0275926 A1 | 9/2014 | Scott | |
| 2014/0288389 A1 | 9/2014 | Gharib | |
| 2014/0303452 A1 | 10/2014 | Ghaffari | |
| 2015/0012066 A1 | 1/2015 | Underwood | |
| 2015/0088029 A1 | 3/2015 | Wybo | |
| 2015/0088030 A1 | 3/2015 | Taylor | |
| 2015/0112325 A1 | 4/2015 | Whitman | |
| 2015/0202395 A1 | 7/2015 | Fromentin | |
| 2015/0238260 A1 | 8/2015 | Nau, Jr. | |
| 2015/0250423 A1 | 9/2015 | Hacker | |
| 2015/0311607 A1 | 10/2015 | Ding | |
| 2015/0380511 A1* | 12/2015 | Irsigler | H01L 29/513 257/295 |
| 2016/0000382 A1 | 1/2016 | Jain | |
| 2016/0015299 A1 | 1/2016 | Chan | |
| 2016/0038072 A1 | 2/2016 | Brown | |
| 2016/0038073 A1 | 2/2016 | Brown | |
| 2016/0038074 A1 | 2/2016 | Brown | |
| 2016/0135834 A1 | 5/2016 | Bleich | |
| 2016/0174861 A1 | 6/2016 | Cadwell | |
| 2016/0199659 A1 | 7/2016 | Jiang | |
| 2016/0235999 A1 | 8/2016 | Bogdan | |
| 2016/0262699 A1 | 9/2016 | Goldstone | |
| 2016/0270679 A1 | 9/2016 | Cameron | |
| 2016/0287112 A1 | 10/2016 | McFarlin | |
| 2016/0287861 A1 | 10/2016 | McFarlin | |
| 2016/0317053 A1 | 11/2016 | Srivastava | |
| 2016/0339241 A1* | 11/2016 | Hargrove | A61N 1/32 |
| 2017/0056643 A1* | 3/2017 | Herb | A61N 1/0456 |
| 2017/0231508 A1* | 8/2017 | Edwards | H04J 3/0667 600/301 |
| 2017/0273592 A1 | 9/2017 | Sterrantino | |
| 2018/0345004 A1 | 12/2018 | McFarlin | |
| 2019/0350485 A1 | 11/2019 | Sterrantino | |

FOREIGN PATENT DOCUMENTS

| | | |
|---|---|---|
| AU | 607977 B2 | 3/1991 |
| AU | 2005269287 A1 | 2/2006 |
| AU | 2006217448 A1 | 8/2006 |
| AU | 2003232111 B2 | 10/2008 |
| AU | 2004263152 B2 | 8/2009 |
| AU | 2005269287 B2 | 5/2011 |
| AU | 2008236665 B2 | 8/2013 |
| AU | 2012318436 A1 | 4/2014 |
| AU | 2016244152 A1 | 11/2017 |
| AU | 2016244152 B2 | 12/2018 |
| AU | 2019201702 A1 | 4/2019 |
| BR | 9604655 C1 | 12/1999 |
| BR | 0609144 A2 | 2/2010 |
| CA | 2144211 C | 5/2005 |
| CA | 2229391 C | 9/2005 |
| CA | 2574845 A1 | 2/2006 |
| CA | 2551185 C | 10/2007 |
| CA | 2662474 A1 | 3/2008 |
| CA | 2850784 A1 | 4/2013 |
| CA | 2769658 C | 1/2016 |
| CA | 2981635 A1 | 10/2016 |
| CN | 101018585 A | 8/2007 |
| CN | 100571811 C | 12/2009 |
| CN | 104066396 A | 9/2014 |
| CN | 103052424 B | 12/2015 |
| CN | 104080509 B | 9/2017 |
| CN | 104717996 B | 1/2018 |
| CN | 107666939 A | 2/2018 |
| CN | 111419179 A | 7/2020 |
| DE | 2753109 A1 | 6/1979 |
| DE | 2831313 A1 | 2/1980 |
| DE | 8803153 U1 | 6/1988 |
| DE | 3821219 C1 | 8/1989 |
| DE | 29510204 U1 | 8/1995 |
| DE | 19530869 A1 | 2/1997 |
| DE | 29908259 U1 | 7/1999 |
| DE | 19921279 C1 | 11/2000 |
| DE | 19618945 C2 | 2/2003 |
| EP | 0161895 A2 | 11/1985 |
| EP | 298268 | 1/1989 |
| EP | 0719113 A1 | 7/1996 |
| EP | 0759307 A2 | 2/1997 |
| EP | 0836514 A2 | 4/1998 |
| EP | 890341 | 1/1999 |
| EP | 972538 | 1/2000 |
| EP | 1656883 A1 | 5/2006 |
| EP | 1115338 B1 | 8/2006 |
| EP | 1804911 A1 | 7/2007 |
| EP | 1534130 A4 | 9/2008 |
| EP | 1804911 B1 | 1/2012 |
| EP | 2481338 A3 | 9/2012 |
| EP | 2763616 A1 | 8/2014 |
| EP | 1385417 B1 | 4/2016 |
| EP | 1680177 B1 | 4/2017 |
| EP | 3277366 A1 | 2/2018 |
| ES | 2725489 T3 | 9/2019 |
| FI | 73878 C | 12/1987 |
| FR | 2624373 A1 | 6/1989 |
| FR | 2624748 B1 | 10/1995 |
| FR | 2796846 A1 | 2/2001 |

(56) References Cited

FOREIGN PATENT DOCUMENTS

| | | |
|---|---|---|
| FR | 2795624 B1 | 9/2001 |
| FR | 2835732 B1 | 11/2004 |
| GB | 1534162 A | 11/1978 |
| GB | 2049431 A | 12/1980 |
| GB | 2052994 A | 2/1981 |
| GB | 2452158 A | 2/2009 |
| GB | 2519302 B | 4/2016 |
| IT | 1221615 B | 7/1990 |
| JP | H0723964 A | 1/1995 |
| JP | 2000028717 A | 1/2000 |
| JP | 3188437 B2 | 7/2001 |
| JP | 2000590531 A | 8/2003 |
| JP | 2003524452 A | 8/2003 |
| JP | 2004522497 A | 7/2004 |
| JP | 2008508049 A | 3/2008 |
| JP | 4295086 B2 | 7/2009 |
| JP | 4773377 B2 | 9/2011 |
| JP | 4854900 B2 | 1/2012 |
| JP | 4987709 B2 | 7/2012 |
| JP | 5132310 B2 | 1/2013 |
| JP | 2014117328 A | 6/2014 |
| JP | 2014533135 A | 12/2014 |
| JP | 6145916 B2 | 6/2017 |
| JP | 2018514258 A | 6/2018 |
| JP | 2018514258 A5 | 5/2019 |
| JP | 6749338 B2 | 9/2020 |
| KR | 100632980 B1 | 10/2006 |
| KR | 1020070106675 A | 11/2007 |
| KR | 100877229 B1 | 1/2009 |
| KR | 20140074973 A | 6/2014 |
| KR | 1020170133499 A | 12/2017 |
| KR | 102092583 B1 | 3/2020 |
| KR | 1020200033979 A | 3/2020 |
| NZ | 541889 A | 4/2010 |
| SE | 467561 B | 8/1992 |
| SE | 508357 C2 | 9/1998 |
| WO | 1999037359 A1 | 7/1999 |
| WO | 2000038574 A1 | 7/2000 |
| WO | 2000066217 A1 | 11/2000 |
| WO | 2001037728 A1 | 5/2001 |
| WO | 2001078831 A2 | 10/2001 |
| WO | 2001087154 A1 | 11/2001 |
| WO | 2001093748 A2 | 12/2001 |
| WO | 2002082982 A1 | 10/2002 |
| WO | 2003005887 A2 | 1/2003 |
| WO | 2003034922 A1 | 5/2003 |
| WO | 2003094744 A1 | 11/2003 |
| WO | 2004064632 A1 | 8/2004 |
| WO | 2005030318 A1 | 4/2005 |
| WO | 2006015069 A1 | 2/2006 |
| WO | 2006026482 A2 | 3/2006 |
| WO | 2006042241 A2 | 4/2006 |
| WO | 2006113394 A2 | 10/2006 |
| WO | 2008002917 A2 | 1/2008 |
| WO | 2008005843 A2 | 1/2008 |
| WO | 2008097407 A2 | 8/2008 |
| WO | 2009051965 A1 | 4/2009 |
| WO | 2010090835 A1 | 8/2010 |
| WO | 2011014598 A1 | 2/2011 |
| WO | 2011150502 A2 | 12/2011 |
| WO | 2013019757 A2 | 2/2013 |
| WO | 2013052815 A1 | 4/2013 |
| WO | 2013151770 A1 | 10/2013 |
| WO | 2015069962 A1 | 5/2015 |
| WO | 2016160477 A1 | 10/2016 |

OTHER PUBLICATIONS

Ott, "Noise Reduction Techniques in Electronic Systems" Second Edition; John Wiley & Sons, p. 62, 1988.
Stecker et al. "Strategies for minimizing 60 Hz pickup during evoked potential recording", Electroencephalography and clinical Neurophysiology 100 (1996) 370-373.
Wood et al. "Comparative analysis of power-line interference between two-or three-electrode biopotential amplifiers" Biomedical Engineering, Med. & Biol. Eng. & Comput., 1995, 33, 63-68.
Clements, et al., "Evoked and Spontaneous Electromyography to Evaluate Lumbosacral Pedicle Screw Placement", 21 (5):600-604 (1996).
Danesh-Clough, et al., "The Use of Evoked EMG in Detecting Misplaced Thoracolumbar Pedicle Screws", 26(12):1313-1316 (2001).
Dezawa et al., "Retroperitoneal Laparoscopic Lateral Approach to the Lumbar Spine: A New Approach, Technique, and Clinical Trial", Journal of Spinal Disorders 13(2):138-143 (2000).
Dickman, et al., "Techniques in Neurosurgery", National Library of Medicine, 3 (4) 301-307 (1997).
Epstein, et al., "Evaluation of Intraoperative Somatosensory-Evoked Potential Monitoring During 100 Cervical Operations", 18(6):737-747 (1993), J.B. Lippincott Company.
Glassman, et al., "A Prospective Analysis of Intraoperative Electromyographic Monitoring of Pedicle Screw Placement with Computed Tomographic Scan Confirmation", 20(12):1375-1379.
Goldstein, et al., "Minimally Invasive Endoscopic Surgery of the Lumbar Spine", Operative Techniques in Orthopaedics, 7 (1):27-35 (1997).
Greenblatt, et al., "Needle Nerve Stimulator-Locator", 41 (5):599-602 (1962).
H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18 (8):626-631 (1996).
Bergey, et al., "Endoscopic Lateral Transpsoas Approach to the Lumbar Spine", Spine 29 (15):1681-1688 (2004).
Holland, "Spine Update, Intraoperative Electromyography During Thoracolumbar Spinal Surgery", 23 (17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. 1-31 Mar. 20, 1998, The Magstim Company Limited.
Kevin T. Foley, et al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et al., "Minimally Invasive Vertebral Replacement with Cages in Thoracic and Lumbar Spine", European Journal of Trauma, 2001, No. 6, pp. 292-300.
Lenke, et al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
MaGuire, et al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et al., "The AnteroLateral transPsoatic Approach (ALPA), A New Technique for Implanting Prosthetic Disc-Nucleus Devices", 16 (4):398-404 (2003).
Michael R. Isley, et al., "Recent Advances in Intraoperative Neuromonitoring of Spinal Cord Function: Pedicle Screw Stimulation Techniques", Am. J. End Technol. 37:93-126 (1997).
Minahan, et al., "The Effect of Neuromuscular Blockade on Pedicle Screw Stimulation Thresholds" 25(19):2526-2530 (2000).
Pimenta et al., "Implante de prótese de núcleo pulposo: análise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et al., "The NerveSeeker: A System for Automated Nerve Localization", Regional Anesthesia 17:151-162 (1992).

(56) References Cited

OTHER PUBLICATIONS

Reidy, et al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et al., "The usefulness of Electrical Stimulation for Assessing Pedicle Screw Placements", Journal of Spinal Disorders, 13 (4):283-289 (2000).
U.Schick, et al., "Microendoscopic lumbar discectomy versus open surgery: an intraoperative EMG study", pp. 20-26, Published online: Jul. 31, 2001 © Springer-Verlag 2001.
Bose, et al., "Neurophysiologic Monitoring of Spinal Nerve Root Function During Instrumented Posterior Lumbar Spine Surgery", 27 (13):1440-1450 (2002).
Vaccaro, et al., "Principles and Practice of Spine Surgery", Mosby, Inc. ©2003, Chapter 21, pp. 275-281.
Vincent C. Traynelis, "Spinal arthroplasty", Neurosurg Focus 13 (2):1-7. Article 10, (2002).
Welch, et al., "Evaluation with evoked and spontaneous electromyography during lumbar instrumentation: a prospective study", J Neurosurg 87:397-402, (1997).
Zouridakis, et al., "A Concise Guide to Intraoperative Monitoring", Library of Congress card No. 00-046750, Chapters, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al., Electrical characteristics of peripheral nerve stimulators, implications for nerve localization, Dept. of Anesthesia, University of Cincinnati College of Medicine, Cincinnati, OH 45267, pp. 73-77.
Deletis et al., "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Butterworth et al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et al., "Threshold-level repetitive transcranial electrical stimulation for intraoperative monitoring of central motor conduction", J. Neurosurg 95:161-168 (2001).
Calancie, et al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
Aage R. Møller, "Intraoperative Neurophysiologic Monitoring", University of Pittsburgh, School of Medicine Pennsylvania, © 1995 by Harwood Academic Publishers GmbH.
Urmey "Using the nerve stimulator for peripheral or plexus nerve blocks" Minerva Anesthesiology 2006; 72:467-71.
Review of section 510(k) premarket notification for "K013215: NuVasive NeuroVision JJB System", Department of Health and Human Services, FDA, Oct. 16, 2001.
International Search Report for PCT/US2005/026692, dated Nov. 16, 2005.
International Search Report for PCT/US2016/023903, dated Sep. 6, 2016.

* cited by examiner

APPARATUS AND METHOD FOR POLYPHASIC MULTI-OUTPUT CONSTANT-CURRENT AND CONSTANT-VOLTAGE NEUROPHYSIOLOGICAL STIMULATION

CROSS-REFERENCE

The present application relies on U.S. Patent Provisional Application No. 62/667,028, entitled "Systems and Methods for Neurophysiological Stimulation" and filed on May 4, 2018, for priority, which is herein incorporated by reference in its entirety.

FIELD

The present specification is related generally to the field of neurophysiological stimulation. More specifically, the present specification is related to a stimulation module and a corresponding intraoperative neurophysiological monitoring software engine that enables a user to select from any combination of nine outputs and a plurality of stimulation variables using software controls to elicit an optimal neurological response.

BACKGROUND

Intraoperative neurophysiological monitoring (IONM) is a diagnostic process that identifies, maps, and monitors neural structures in accordance with their functions with a goal of preserving the structural integrity of these neural structures during physically invasive procedures such as surgery.

In some methods, identifying, mapping and monitoring neural structures comprises applying electrical stimulation at or near an area where the target neural structures are believed to be located. Application of the electrical stimulation is transmitted through the nerve structures to excite the associated muscle(s). An electrical impulse is generated in the muscle(s), as a result of the excitation, that can be sensed using recording electrodes, thereby indicating presence of a neural structure to a surgeon. For example, cortical stimulation mapping (CSM) is a type of electrocorticography that involves a physically invasive procedure and aims to localize the function of specific brain regions through direct electrical stimulation of the cerebral cortex.

Conventional nerve integrity monitoring systems pose limitations when used across varied surgical procedures and accompanied neuro-stimulation scenarios. By way of example, a majority of prior art nerve integrity monitoring systems only have a limited number of outputs or channels for delivering stimulation to a plurality of neural regions thereby limiting the ability to simultaneously stimulate multiple nerves or multiple branches of single nerves. This is a critical limitation as it necessitates frequent manual intervention, such as having to move the connections of stimulation components (for example, electrodes and probes) to change the location of the delivered stimulus on a patient's anatomy.

Additional drawbacks of prior art nerve integrity monitoring systems include: stimulators that can function in a single mode, that is, functionality in either constant-voltage or constant-current configuration mode but not both; the use of single or biphasic pulses and pulse trains requiring a separate priming stimulus followed by a test stimulus; a lack of synchronization with facilitation stimulators; a lack of availability of fixed output or channel pairs constraining the flexibility in determining the best stimulation site; a limited pulse width (such as, for example, of 75 microseconds or less) and no electrode impedance measurement.

As a result of these limitations, prior art nerve integrity monitoring systems are associated with various disadvantages including the need for additional operational steps which increase the duration of the surgical procedures to the detriment of patients and medical personnel, an increased complexity and confusion associated with intraoperative neural monitoring, a requirement for human and/or mechanical intervention, and an inability to efficiently integrate multiple neural stimulation and monitoring modalities.

Thus, there is a need for systems and methods that provide versatility of operation and function to a user by integrating a plurality of stimulation modalities. There is also a need for systems and methods that enable a user to stimulate the neurological system with minimal, less frequent and more streamlined manual, semi-automatic, automatic and/or electromechanical intervention.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses an intraoperative neurophysiological monitoring (IONM) system, comprising: a computing device executing an IONM software engine, said computing device comprising at least one processor, at least one non-transitory memory, one or more input devices, and one or more output devices, wherein said computing device is in data communication with one or more databases; a console in electrical communication with the computing device; a stimulation module comprising a housing and connected to a distal end of a cable, a proximal end of said cable being connected to the console, wherein said stimulation module comprises nine output ports; one or more stimulation components connected to one or more output ports of the stimulation module; and a plurality of sensing electrodes connected to the console.

The present specification also discloses a method of transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of stimulation components and a plurality of recording electrodes, the method comprising: positioning at least one recording electrode on a patient; connecting said plurality of stimulation components to at least one port on said stimulation module; positioning said plurality of stimulation components on a patient's head; activating, using said IONM software engine, at least one port; delivering stimulation to the patient; and recording a stimulatory response on the patient.

The present specification also discloses a stimulation module configured to generate and deliver an electrical stimulus comprising at least one stimulation pulse, the stimulation module comprising: a plurality of output ports adapted to connect to a plurality of stimulation electrodes; a controller, wherein the controller is configured to simultaneously activate any combination of the plurality of output ports and is configured to set any of the plurality of output ports to being either an anode or a cathode; an adjustable voltage converter, wherein the adjustable voltage converter is configured to raise or lower an output supply voltage; a pulse generator comprising: a constant current sink adapted to enable a setting of an intensity of an output current of the stimulation module; a current intensity digital-to-analog converter adapted to generate voltage for the current sink that is proportional to the set output current intensity; trigger logic adapted to enable the stimulation module to switch between a plurality of current intensities; and a current sense circuit to measure delivered current; and a constant voltage source adapted to enable a setting of an intensity of an output voltage of the stimulation module.

Optionally, the stimulation module further comprises an impedance circuit comprising an impedance voltage generator, an impedance pulse generator, and an impedance sense circuit, wherein the impedance circuit is configured to measure impedance of the plurality of stimulation electrodes.

Optionally, the adjustable voltage converter is configured to adjust a voltage to raise or lower the output supply voltage.

Optionally, the stimulation module is operably connected to a computing device of an intraoperative neurophysiological monitoring (IONM) system wherein the controller comprises an IONM software engine adapted to execute in the computing device.

Optionally, the plurality of outputs ports comprise at least nine output ports.

Optionally, the adjustable voltage converter is a DC to DC voltage converter and capable of converting a voltage in a range of 200 to 1200 volts. Optionally, the adjustable voltage converter comprises a digital-to-analog converter wherein the digital-to-analog converter is configured to vary a voltage in a feedback loop of the DC-DC converter thereby causing a DC-DC controller to adjust a switching duty cycle to raise or lower the output supply voltage.

Optionally, the constant voltage source generates an output voltage using an emitter follower field-effect transistor. Optionally, a gate voltage of the field-effect transistor is set by a digital-to-analog converter wherein the output voltage is proportional to the digital-to-analog converter voltage.

Optionally, the current sink comprises two digital-to-analog converters and a high speed amplifier to control separate phases of the pulse.

Optionally, an output current is set by the digital-to-analog converter voltage at an input of an amplifier. Optionally, the setting of the output current is adapted to force a voltage across a ground referenced transistor at an output.

Optionally, the pulse generator comprises a field-effect transistor and an amplifier, wherein the pulse generator is adapted to limit and sense an impedance current.

Optionally, the plurality of output ports are configured to be controlled by a gate drive optocoupler and H-Bridge transformer driver.

Optionally, the controller is configured to monitor voltage values on a first side and a second side of a high voltage rail, wherein the controller is configured to monitor a value of current, and wherein the controller is configured to output a measurement of a delivered pulse based upon the monitored voltage values and the monitored current value.

Optionally, the controller is adapted to use the monitored voltage values and the monitored current value to compute an on-the-fly impedance value.

Optionally, the stimulation module is configured to be in time synchronization with a plurality of facilitation stimulators and a plurality of recording electrodes and wherein the plurality of facilitation stimulators and the plurality of recording electrodes are in data communication with a computing device of an intraoperative neurophysiological monitoring (IONM) system. Optionally, the time synchronization is achieved using a digital timing signal and coordination of a timestamp by the computing device.

Optionally, the at least one stimulation pulse is polyphasic.

Optionally, the stimulation module is configured to generate the at least one stimulation pulse having a voltage output up to 1000 Volts and a current of 1.5 Amps as any combination of single pulses or pulse trains.

Optionally, the controller is configured to modulate at least one of a plurality of stimulation parameters of the at least one stimulation pulse.

Optionally, the stimulation module further comprises an impedance circuit configured to measure an impedance of the plurality of stimulation electrodes based upon a plurality of pulses, wherein the plurality of pulses is a generated by combination of one of the plurality of output ports being configured as an anode and remaining ones of the plurality of output ports being configured as cathodes.

Optionally, the stimulation module is configured to operate in a constant voltage mode wherein the output current is limited in the constant voltage mode.

Optionally, the stimulation module is configured to operate in a constant current mode wherein the output voltage is limited in the constant current mode.

Optionally, the stimulation module further comprises first and second safety circuits.

Optionally, the stimulation module is configured to be powered down if communication is lost between the stimulation module and a computing device of an intraoperative neurophysiological monitoring (IONM) system.

The present specification also discloses an intraoperative neurophysiological monitoring (IONM) system, comprising: a computing device executing an IONM software engine, said computing device comprising at least one processor, at least one non-transitory memory, one or more input devices, and one or more output devices, wherein said computing device is in data communication with one or more databases; a console in electrical communication with the computing device; a stimulation module comprising a housing and connected to a distal end of a cable, a proximal end of said cable being connected to the console, wherein said stimulation module comprises nine output ports; one or more stimulation components connected to one or more output ports of the stimulation module; and a plurality of sensing electrodes connected to the console.

The present specification also discloses a method of transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of stimulation components and a plurality of recording electrodes, the method comprising: positioning at least one recording electrode on a patient; connecting said plurality of stimulation components to at least one port on said stimulation module; positioning said plurality of stimulation components on a patient's head; activating, using said IONM software engine, at least one port; delivering stimulation to the patient; and recording a stimulatory response on the patient.

Optionally, a recording electrode is positioned on the patient's right leg, wherein said plurality of stimulation components are connected to six ports of said stimulation module, wherein first and second ports are activated as anode and cathode respectively, and wherein stimulation is delivered in accordance with a first stimulation protocol. Optionally, the first stimulation protocol comprises a constant voltage of 100V having a train of 5 pulses and an inter-stimulus interval (ISI) of 2 ms. Optionally, if no stimulatory response is recorded at the patient's right leg then the method further comprises the steps of: increasing an area of stimulation by adding a third port as an anode; activating said first, second and third ports; and delivering stimulation to the patient using said first stimulation protocol. Optionally, the method further comprises increasing the constant voltage intensity to achieve a larger stimulatory response; activating said first, second and third ports; and delivering stimulation to the patient using a second stimulation protocol. Optionally, the second stimulation protocol comprises said increased constant voltage of 200V having a train of 5 pulses and an inter-stimulus interval (ISI) of 2 ms.

Optionally, recording electrodes are positioned on the patient's right arm and right leg, wherein said plurality of stimulation components are connected to six ports of said stimulation module, wherein first and second ports are activated as anode and cathode respectively, and wherein stimulation is delivered in accordance with a first stimulation protocol. Optionally, the first stimulation protocol comprises a constant voltage of 100V having a train of 5 pulses and an inter-stimulus interval (ISI) of 2 ms. Optionally, if no stimulatory response is recorded at the patient's right arm or leg then the method further comprises the steps of: increasing an area of stimulation by adding a third port as an anode; activating said first, second and third ports; and delivering stimulation to the patient using said first stimulation protocol. Optionally, said method further comprises changing a mode of stimulation to constant-current to reduce effects of electrode impedance and increase stimulatory response; activating said first, second and third ports; and delivering stimulation to the patient using a second stimulation protocol. Optionally, the second stimulation protocol comprises constant-current at an amplitude of 100 mA having a train of 5 pulses and an inter-stimulus interval (ISI) of 2 ms.

Optionally, recording electrodes are positioned on the patient's left and right legs, wherein said plurality of stimulation components are connected to six ports of said stimulation module, wherein first and second ports are activated as anode and cathode, respectively, during a first phase of a biphasic pulse and third and second ports are activated as anode and cathode, respectively, during a second phase of the biphasic stimulation pulse, and wherein stimulation is delivered in accordance with a first stimulation protocol.

Optionally, the first stimulation protocol comprises a constant voltage of 100V having a train of 5 pulses and an inter-stimulus interval (ISI) of 2 ms. Optionally, if no stimulatory response is recorded at the patient's left and right legs then the method further comprises the steps of: increasing an area of stimulation by adding fourth and fifth ports as anodes; activating said first, fourth and second ports during the first phase and said third, fifth and second ports during the second phase; and delivering stimulation to the patient using said first stimulation protocol.

Optionally, the method further comprises increasing the constant voltage intensity to achieve a larger stimulatory response; activating said first, fourth and second ports during the first phase and said third, fifth and second ports during the second phase; and delivering stimulation to the patient using a second stimulation protocol. Optionally, said second stimulation protocol comprises said increased constant voltage of 200V having a train of 5 pulses and an inter-stimulus interval (ISI) of 2 ms.

Optionally, recording electrodes are positioned on the patient's left and right arms as well as left and right legs, wherein said plurality of stimulation components are connected to six ports of said stimulation module, wherein during a first phase of a biphasic stimulation pulse first and second ports are activated as anodes and third and fourth ports are activated as cathodes and during a second phase of the biphasic stimulation pulse third and fourth ports are activated as anodes and first and second ports are activated as cathodes, and wherein stimulation is delivered in accordance with a first stimulation protocol. Optionally, the first stimulation protocol comprises a constant voltage of 100V having a train of 5 pulses and an inter-stimulus interval (ISI) of 2 ms. Optionally, if no stimulatory response is recorded at the patient's left and right arms as well as left and right legs then the method further comprises the steps of: changing a mode of stimulation to constant-current to reduce effects of electrode impedance and increase stimulatory response; activating said first and second ports as anodes and third and fourth ports as cathodes during the first phase of the biphasic stimulation pulse and activating third and fourth ports as anodes and first and second ports as cathodes during the second phase of the biphasic stimulation pulse; and delivering stimulation to the patient using a second stimulation protocol. Optionally, the second stimulation protocol comprises said constant current of amplitude 120 mA having a train of 5 pulses and an inter-stimulus interval (ISI) of 2 ms.

The present specification also discloses a method of facilitation stimulation for transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of facilitation stimulators, a plurality of stimulation components and a plurality of recording electrodes, the method comprising: positioning at least one recording electrode on a patient; connecting said plurality of stimulation components to at least one port on said stimulation module; positioning said plurality of stimulation components on a patient's head; positioning at least one facilitation stimulator on the patient; activating, using said IONM software engine, said at least one facilitation stimulator; using the facilitation stimulator to deliver facilitation stimulus to at least one nerve structure of the patient, wherein said facilitation stimulation is delivered at a first stimulation protocol; modulating at least one parameter of the first stimulation protocol; activating, using said IONM software engine, at least one port; delivering stimulation to the patient at a second stimulation protocol; and recording a stimulatory response on the patient.

Optionally, said at least one recording electrode is positioned on the patient's right leg, wherein said plurality of stimulation components are connected to six ports of said stimulation module, wherein said at least one facilitation stimulator is positioned on the patient's right leg, wherein the nerve structure is a right posterior tibial nerve, wherein the first stimulation protocol comprises constant current at an amplitude of 25 mA having a train of 3 pulses and an inter-stimulus interval of 2 ms, wherein the inter-train interval is modulated in a range of 40 ms to 50 ms, wherein first and second ports are activated as anode and cathode, respectively, and wherein the second stimulation protocol comprises constant voltage at an amplitude of 80V having a train of 5 pulses and an inter-stimulus interval of 2 ms.

Optionally, said plurality of recording electrodes are positioned on the patient's left and right arms as well left and right legs, wherein said plurality of stimulation components are connected to six ports of said stimulation module, wherein said plurality of facilitation stimulators are positioned on the patient's left and right arms as well left and right legs, wherein the nerve structures are left and right median nerves as well as left and right posterior tibial nerve, wherein the first stimulation protocol comprises constant current at an amplitude of 25 mA having a train of 3 pulses and an inter-stimulus interval of 2 ms, wherein the inter-train interval is modulated in a range of 40 ms to 50 ms, wherein during a first phase of a biphasic pulse first and second ports are activated as anodes while third and fourth ports are activated as cathodes and during a second phase of the biphasic pulse third and fourth ports are activated as anodes while first and second ports are activated as cathodes, and wherein the second stimulation protocol comprises constant current at an amplitude of 80 mA having a train of 5 pulses and an inter-stimulus interval of 2 ms.

The present specification also discloses a method of transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of stimulation components and a plurality of recording electrodes, the method comprising: positioning a recording electrode on a patient's right leg; connecting said plurality of stimulation components to six ports on said stimulation module; positioning said plurality of stimulation components on a patient's head; activating, using said IONM software engine, first and second ports as anode and cathode respectively; delivering stimulation to the patient at a first stimulation protocol, wherein said first protocol comprises a constant voltage of 100V having a train of 5 pulses and an inter-stimulus interval of 2 ms; recording a first stimulatory response on the patient, wherein said first response is nil; increasing an area of stimulation by adding a third port as an anode; activating, using said IONM software engine, said first, second and third ports; delivering stimulation to the patient using said first stimulation protocol; recording a second stimulatory response on the patient; increasing a constant voltage intensity of stimulation to achieve a third stimulatory response; activating said first, second and third ports; delivering stimulation to the patient using a second stimulation protocol, wherein said second stimulation protocol comprises said increased constant voltage intensity of 200V having a train of 5 pulses and an inter-stimulus interval of 2 ms; and recording the third stimulatory response on the patient, wherein said third response is greater than said second response.

The present specification also discloses a method of transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of stimulation components and a plurality of recording electrodes, the method comprising: positioning a recording electrode on a patient's right arm and right leg; connecting said plurality of stimulation components to six ports on said stimulation module; positioning said plurality of stimulation components on a patient's head; activating, using said IONM software engine, first and second ports as anode and cathode respectively; delivering stimulation to the patient at a first stimulation protocol, wherein said first protocol comprises a constant voltage of 100V having a train of 5 pulses and an inter-stimulus interval of 2 ms; recording a first stimulatory response on the patient, wherein said first response corresponds to no response at the right arm; increasing an area of stimulation by adding a third port as an anode; activating, using said IONM software engine, said first, second and third ports; delivering stimulation to the patient using said first stimulation protocol; recording a second stimulatory response on the patient; changing a mode of stimulation to constant current to reduce effects of electrode impedance and to achieve a third stimulatory response; activating said first, second and third ports; delivering stimulation to the patient using a second stimulation protocol, wherein said second stimulation protocol comprises said constant current of 100 mA having a train of 5 pulses and an inter-stimulus interval of 2 ms; and recording the third stimulatory response on the patient, wherein said third response is greater than said second response.

The present specification also discloses a method of transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of stimulation components and a plurality of recording electrodes, the method comprising: positioning a recording electrode on a patient's left and right legs; connecting said plurality of stimulation components to six ports on said stimulation module; positioning said plurality of stimulation components on a patient's head; using said IONM software engine to activate first and second ports as anode and cathode respectively during a first phase of a biphasic pulse and activate third and second ports as anode and cathode respectively during a second phase of the biphasic pulse; delivering stimulation to the patient at a first stimulation protocol, wherein said first protocol comprises a constant voltage of 100V having a train of 5 pulses and an inter-stimulus interval of 2 ms; recording a first stimulatory response on the patient, wherein said first response corresponds to no response at the left and right legs; increasing an area of stimulation by adding a fourth and fifth ports; using said IONM software engine to activate said first and fourth ports as anodes while said second port as cathode during the first phase of the biphasic pulse and activate said third and fifth ports as anodes while said second port as cathode during the second phase of the biphasic pulse; delivering stimulation to the patient using said first stimulation protocol; recording a second stimulatory response on the patient; increasing a voltage intensity of stimulation to achieve a third stimulatory response; using said IONM software engine to activate said first and fourth ports as anodes while said second port as cathode during the first phase of the biphasic pulse and activate said third and fifth ports as anodes while said second port as cathode during the second phase of the biphasic pulse; delivering stimulation to the patient using a third stimulation protocol, wherein said third stimulation protocol comprises said increased constant voltage of 200V having a train of 5 pulses and an inter-stimulus interval of 2 ms; and recording the third stimulatory response on the patient, wherein said third response is greater than said second response.

The present specification also discloses a method of transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of stimulation components and a plurality of recording electrodes, the method comprising: positioning a recording electrode on a patient's left and right arms as well as left and right legs; connecting said plurality of stimulation components to six ports on said stimulation module; positioning said plurality of stimulation components on a patient's head; using said IONM software engine to activate first and second ports as anodes and third and fourth ports as cathodes during a first phase of a biphasic pulse and activate third and fourth ports as anodes and first and second ports as cathodes during a second phase of the biphasic pulse; delivering stimulation to the patient at a first stimulation protocol, wherein said first protocol comprises a constant voltage of 100V having a train of 5 pulses and an inter-stimulus interval of 2 ms; recording a first stimulatory response on the patient, wherein said first response corresponds to no response at the left and right arms as well as the left and right legs; changing a mode of stimulation to constant current to reduce effects of electrode impedance and to achieve a second stimulatory response; using said IONM software engine to activate first and second ports as anodes and third and fourth ports as cathodes during a first phase of a biphasic pulse and activate third and fourth ports as anodes and first and second ports as cathodes during a second phase of the biphasic pulse; delivering stimulation to the patient using a second stimulation protocol, wherein said second stimulation protocol comprises said constant current of 120 mA having a train of 5 pulses and an inter-stimulus interval of 2 ms; and recording the second stimulatory response on the patient.

The present specification also discloses a method of facilitation stimulation for transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of facilitation stimulators, a plurality of stimulation components and a plurality of recording electrodes, the method comprising: positioning at least one recording electrode on a patient's right leg; connecting said plurality of stimulation components to six ports on said stimulation module; positioning said plurality of stimulation components on a patient's head; positioning at least one facilitation stimulator on the patient's right leg; activating, using said IONM software engine, said at least one facilitation stimulator; using said IONM software engine to activate said at least one facilitation stimulator and deliver a facilitation stimulus to a right posterior tibial nerve of the patient, wherein said facilitation stimulation is delivered at a first stimulation protocol comprising constant current of 25 mA having a train of 3 pulses and an inter-stimulus interval of 2 ms; modulating the inter-train interval, of the first stimulation protocol, in a range of 40 ms to 50 ms; activating, using said IONM software engine, first and second ports as anode and cathode respectively; delivering stimulation to the patient at a second stimulation protocol comprising constant voltage of 80V having a train of 5 pulses and an inter-stimulus interval of 2 ms; and recording a stimulatory response on the right leg.

The present specification also discloses a method of facilitation stimulation for transcranial electrical stimulation and motor evoked potential (MEP) monitoring during a surgical procedure, said method being implemented using an intraoperative neurophysiological monitoring (IONM) system comprising a computing device capable of executing an IONM software engine, a stimulation module having nine ports, a plurality of facilitation stimulators, a plurality of stimulation components and a plurality of recording electrodes, the method comprising: positioning said plurality of recording electrodes on a patient's left and right arms as well as left and right legs; connecting said plurality of stimulation components to six ports on said stimulation module; positioning said plurality of stimulation components on a patient's head; positioning said plurality of facilitation stimulators on the patient's left and right arms as well as left and right legs; activating, using said IONM software engine, said plurality of facilitation stimulators; using said IONM software engine to activate said at least one facilitation stimulator and deliver facilitation stimulation to left and right median nerves as well as left and right posterior tibial nerves of the patient, wherein said facilitation stimulation is delivered at a first stimulation protocol comprising constant current of 25 mA having a train of 3 pulses and an inter-stimulus interval of 2 ms; modulating the inter-train interval, of the first stimulation protocol, in a range of 40 ms to 50 ms; using said IONM software engine to activate first and second ports as anodes while third and fourth ports as cathodes during a first phase of a biphasic pulse and activate third and fourth ports as anodes while first and second ports as cathodes during a second phase of the biphasic pulse; delivering stimulation to the patient at a second stimulation protocol comprising constant current of 80 mA having a train of 5 pulses and an inter-stimulus interval of 2 ms; and recording stimulatory responses on the left and right arms as well as left and right legs.

The present specification also discloses a stimulation module for delivering electrical stimulus comprising at least one stimulation pulse, said stimulation module being operably connected to a computing device of an intraoperative neurophysiological monitoring (IONM) system, wherein said computing device executes an IONM software engine, said stimulation module comprising: nine output ports to enable connection to a plurality of stimulation electrodes, wherein said IONM software engine can simultaneously activate any combination of said nine output ports and can set all of said nine output ports as anode or cathode; an adjustable 200 to 1200 volt DC-DC converter and a high voltage sense circuit, wherein said DC-DC converter uses a digital-to-analog converter to vary a voltage in a feedback loop of said DC-DC converter thereby causing a DC-DC controller to adjust a switching duty cycle to raise or lower said output supply voltage; a pulse generator comprising: a constant current sink that enables setting an output current intensity of said stimulation module; a current intensity digital-to-analog converter (DAC) for generating voltage for said current sink that is proportional to a requested stimulus current intensity; trigger logic to enable said stimulation module to switch between a plurality of current intensities; and a current sense circuit to measure delivered current; a constant voltage source that enables setting an output voltage intensity of said stimulation module; and an impedance voltage generator functioning in conjunction with an impedance pulse generator and an impedance sense circuit for measuring impedance of said plurality of stimulation electrodes.

Optionally, said constant voltage source generates an output voltage using an emitter follower field-effect transistor whose gate voltage is set by a digital-to-analog converter, and wherein said output voltage is proportional to the digital-to-analog converter voltage.

Optionally, said current sink comprises two digital-to-analog converters and a high speed amplifier to control separate phases of said pulse.

Optionally, an output current is set by the digital-to-analog converter voltage at an input of the high speed amplifier which then forces the voltage across a ground referenced transistor at the output.

Optionally, said pulse generator comprising of a field-effect transistor, fixed impedance and an amplifier, wherein said pulse generator is used to limit and sense an impedance current.

Optionally, said nine output ports are controlled by a gate drive optocoupler and H-Bridge transformer driver.

Optionally, voltage values on both sides of a high voltage rail are monitored along with current value to provide an accurate measurement of a delivered pulse, and wherein said monitored values are used to compute an "on the fly" impedance.

Optionally, said IONM system further comprises a plurality of facilitation stimulators and a plurality of recording electrodes, and wherein said stimulation module, said plurality of facilitation stimulators and said plurality of recording electrodes are in time synchronization with each other.

Optionally, said time synchronization is achieved using a digital timing signal and coordination of a timestamp by said computing device.

Optionally, said at least one stimulation pulse is polyphasic.

Optionally, said electrical stimulus has output up to 1000 Volts and 1.5 Amps, and wherein said electrical stimulus is configurable as any combination of single pulses or pulse trains.

Optionally, at least one of a plurality of stimulation parameters of said electrical stimulus is modulated using said IONM software engine.

Optionally, at least one of said nine output ports can be activated using said IONM software engine.

Optionally, at least one of said output ports is configured as an anode.

Optionally, at least one of said output ports is configured as a cathode anode.

Optionally, said high voltage and current sense circuits enable measurement of said delivered electrical stimulus using voltage dividers, amplifiers and analog-to-digital converters.

Optionally, measurement of electrode impedance is achieved using both successive approximation and averaging of nine pulses, wherein each of said nine pulses is a combination of one output port configured as an anode and the remaining output ports configured as cathodes.

Optionally, said stimulation module is a battery-powered wireless module.

Optionally, said stimulation module is operated in a constant voltage mode, and wherein current is limited in said constant voltage mode.

Optionally, said stimulation module is operated in a constant current mode, and wherein voltage is limited in said constant current mode.

Optionally, said stimulation module further comprises first and second safety circuits.

Optionally, said stimulation module is powered down if communication is lost between said stimulation module and said computing device.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings.

DETAILED DESCRIPTION

Figure 1A:
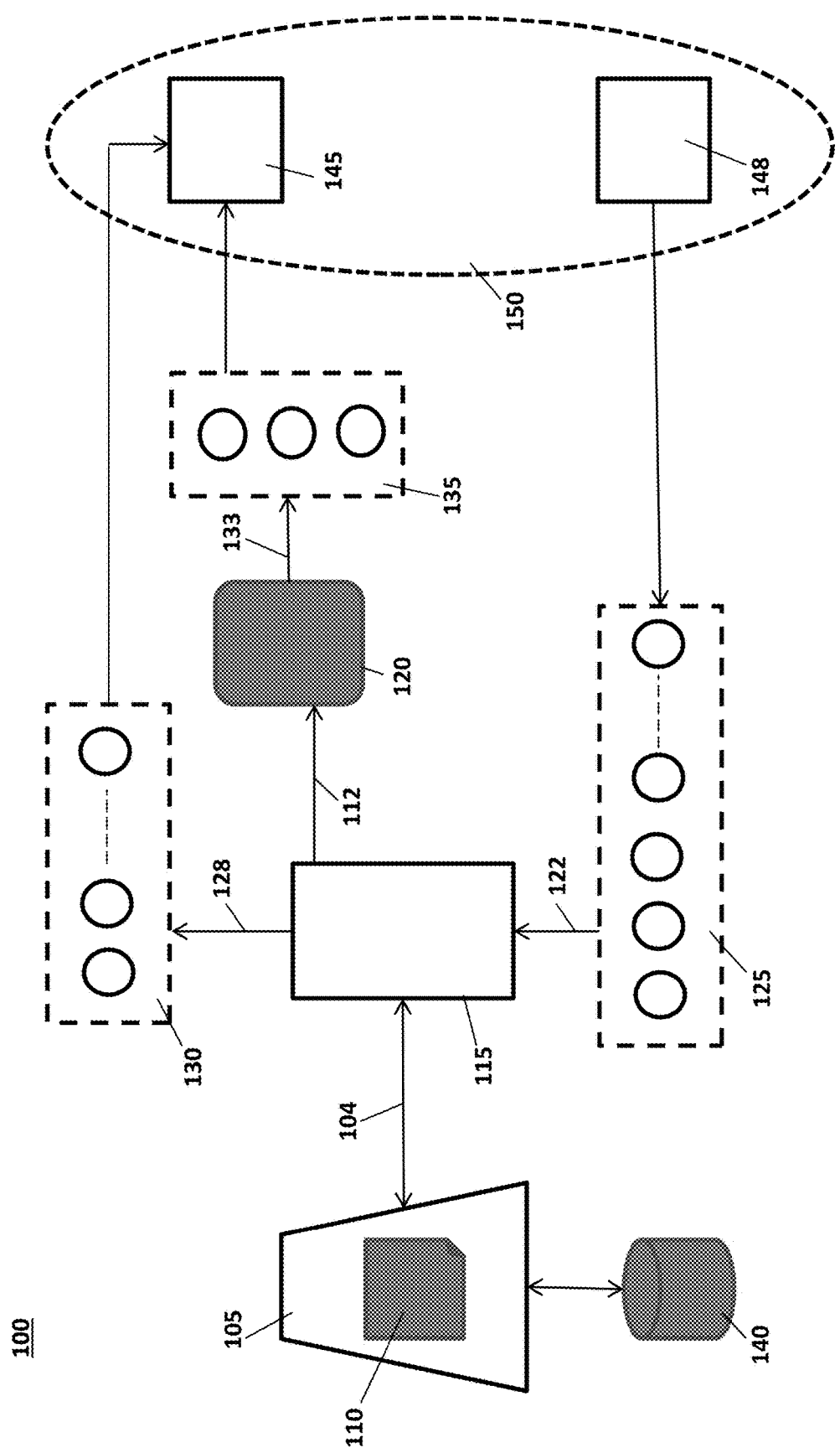
FIG. 1A is a block diagram illustrating an intraoperative neuromonitoring (IONM) system, in accordance with an embodiment of the present specification.

A "computing device" is at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and transmitting data. Each "computing device"

may be coupled to at least one display, which displays information about the patient parameters and the functioning of the system, by means of a GUI. The GUI also presents various menus that allow users to configure settings according to their requirements. The system further comprises at least one processor (not shown) to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

The term 'user' is used interchangeably to refer to a surgeon, neuro-physician, neuro-surgeon, neuro-physiologist, technician or operator of the IONM system and/or other patient-care personnel or staff.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

An Intraoperative Neuro-Monitoring (IONM) System

FIG. 1A is a block diagram illustration of an IONM system 100, in accordance with an embodiment of the present specification. In embodiments, the system 100 enables a stimulation-based assessment of nerve proximity, direction, pathways and/or changes to nerve pathology, health or status during physically invasive procedures. The system 100 comprises a computing device 105 configured to implement or execute an IONM software application or engine 110, at least one multi-connection console 115 connected to the computing device 105 using a cable 104, a stimulation module 120 connected to the console 115 using a cable 112, a plurality of stimulation components 135 such as, but not limited to, subdermal, hooked or corkscrew needle electrodes or surface electrodes adapted to be coupled to the stimulation module 120 simultaneously or in any combination thereof via respective cables 133, a plurality of recording or sensing electrodes 125 connected to the console 115 through respective cables 122 and a plurality of surgical instruments, components and accessories 130 coupled to the console 115 via respective accessory cables 128.

In various embodiments, the computing device 105 comprises at least one processor, at least one non-transitory memory, one or more input devices (such as, but not limited to, keyboard, mouse, touch-screen, camera and combinations thereof) and one or more output devices (such as, but not limited to, display screens, printers, speakers and combinations thereof) all of which may be stand-alone, integrated into a single unit, partially or completely network-based or cloud-based, and not necessarily located in a single physical location. The computing device 105 is in data communication with one or more databases 140 that may be co-located with the computing device 105 or located remotely.

The IONM software application or engine 110 implements a plurality of instructions to: deliver a plurality of stimulation protocols or schedules (stored in the one or more databases 140) through any one, any combination or all of the plurality of stimulation components 135, generate a plurality of graphical user interfaces (GUIs) rendered on one or more display screens (that are coupled to the computing device 105) to display a plurality of MEP (Motor Evoked Potential) activity waveforms sensed by the electrodes 125 and extract a plurality of parameters related thereto and enable user-interaction with the system 100 to perform a plurality of functions such as, but not limited to, selecting and activating/initiating one or more stimulation protocols and modulating one or more stimulation parameters of the protocols. The IONM software application or engine 110 is configured to apply one or more stimulation protocols to one or more nerve structures 145 of a patient 150 through the plurality of stimulation components 135 and acquire and record correspondingly MEP activity through the plurality of electrodes 125 positioned within a plurality of muscle sites or locations 148 of the patient 150.

It should be appreciated by those of ordinary skill in the art that, although described herein with reference to transcranial electrical stimulation (TES) and motor evoked potential monitoring (MEP) during cerebrospinal surgical procedures, the system 100 and related methods or use cases of the present specification have application in a plurality of surgical procedures during which tissue having critical neural structures must be approached, retracted, and/or impinged upon. There is a requirement that such physically invasive procedures be planned and executed while preserving critical neural structures or bundles. It should also be appreciated that, although embodiments have been described herein with reference to MEP activity, the system 100 and related methods or use cases of the present specification may, in various alternate embodiments, use a plurality of different types of neural monitoring modalities such as, for example, triggered electromyography, spontaneous electromyography, mechanomyography, somatosensory evoked potential, nerve conduction velocity and/or train of fours.

The Stimulation Module

Figure 1B:
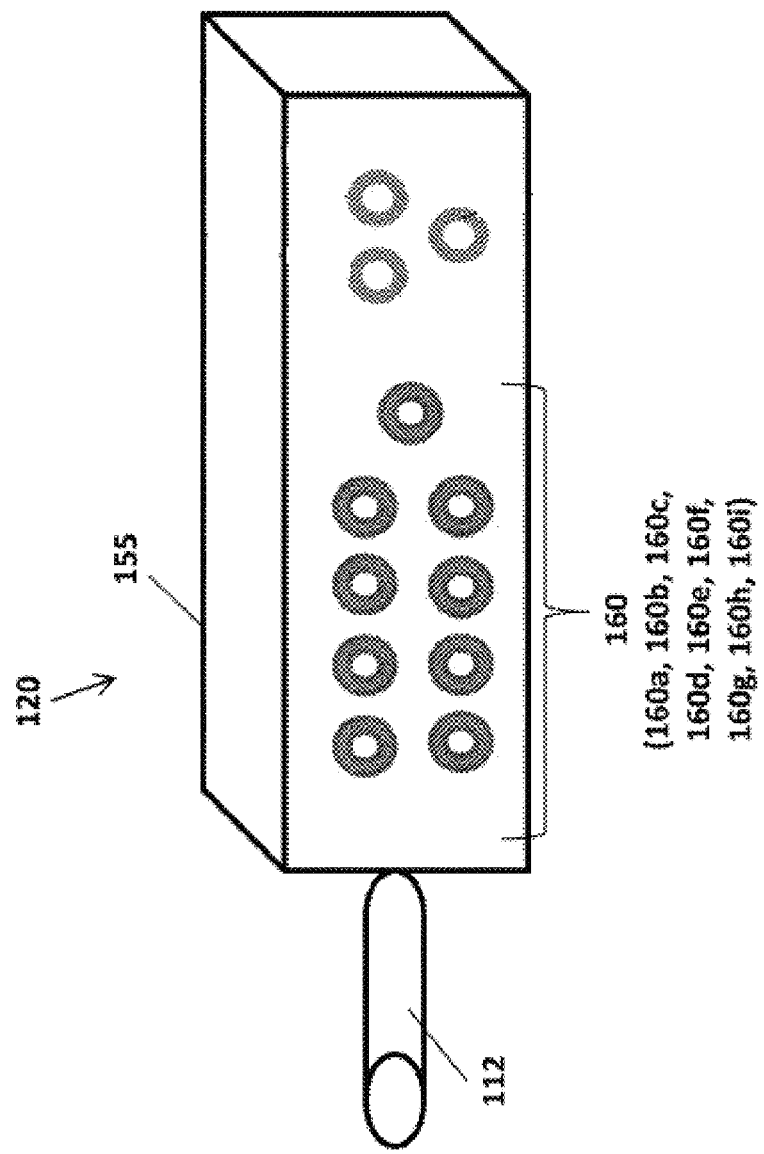
FIG. 1B illustrates a stimulation module, in accordance with an embodiment of the present specification.

FIG. 1B illustrates the stimulation module 120, in accordance with an embodiment of the present specification. The module 120 comprises a housing or enclosure 155 connected, in some embodiments, to a distal end of the electrical cable 112 while a proximal end of the cable 112 is connected to the console 115. In alternate embodiments, the proximal end of the cable 112 may be connected directly to the computing device 105 via a connector such as a D-subminiature connector. In other alternate embodiments, the module 120 may be connected to the console 115 through the electrical cable 112 that serves only to deliver power to the module 120, while the module 120 is in wireless data communication with the computing device 105. Also, in some embodiments, the module 120 is configured as a battery-operated and portable hand-held device.

In embodiments, the module 120 comprises a plurality of output channels or ports 160. In accordance with an embodiment, the plurality of output channels comprise nine ports 160a, 160b, 160c, 160d, 160e, 160f, 160g, 160h, 160i. In accordance with an embodiment, any of the nine ports 160a-160i can be configured and flexibly chosen as any combination of anode or cathode per stimulus thereby allowing user-defined stimuli to be delivered to arbitrary anode and cathode outputs. In one embodiment, a plurality of subdermal needle electrodes are connected to the required number of output ports from the available nine ports 160a-160i.

It should be appreciated that there may be scenarios where one or a combination of stimulation modalities may be of value in a surgical procedure, depending on a stage of a surgical procedure and/or based on what anatomical structure is being stimulated. Because an optimal stimulation paradigm may differ across patients and surgical procedure types, the stimulation module 120 allows the user to easily prepare a varied neuro-stimulation setup, without having to physically move electrodes and/or probes and/or adjust the stimulus paradigm via dials and switches on a device at the computing device or near the operating room table. In accordance with various further aspects of the present specification, the stimulation module 120 delivers polyphasic electrical stimulus with an output of 0 to 1000 Volts, amplitude of 0 to 1.5 Amps and is configurable as any combination of single pulses or multiple pulse trains, enables modulation of one or more of a plurality of stimulation parameters digitally using the IONM software engine 110, is operable as a constant-current or constant-voltage stimulator with current and voltage sensing of delivered stimulus, supports electrode impedance measurement and determination of individual electrode impedance, is tightly synchronized with additional one or more stimulators for neural facilitation, supports transformer-coupled output switching without need for high-side voltage charge pump, is a battery-powered, wireless stimulator and supports a power management scheme, has built-in safety features including redundant circuitry, energy limited power supply, non-stimulating mode with loss of communication, self-diagnostic tests, current and voltage limiting, and includes printed-circuit board spacing and trace management for high energy pulse switching as well as low voltage control signals in a single module.

Figure 2A:
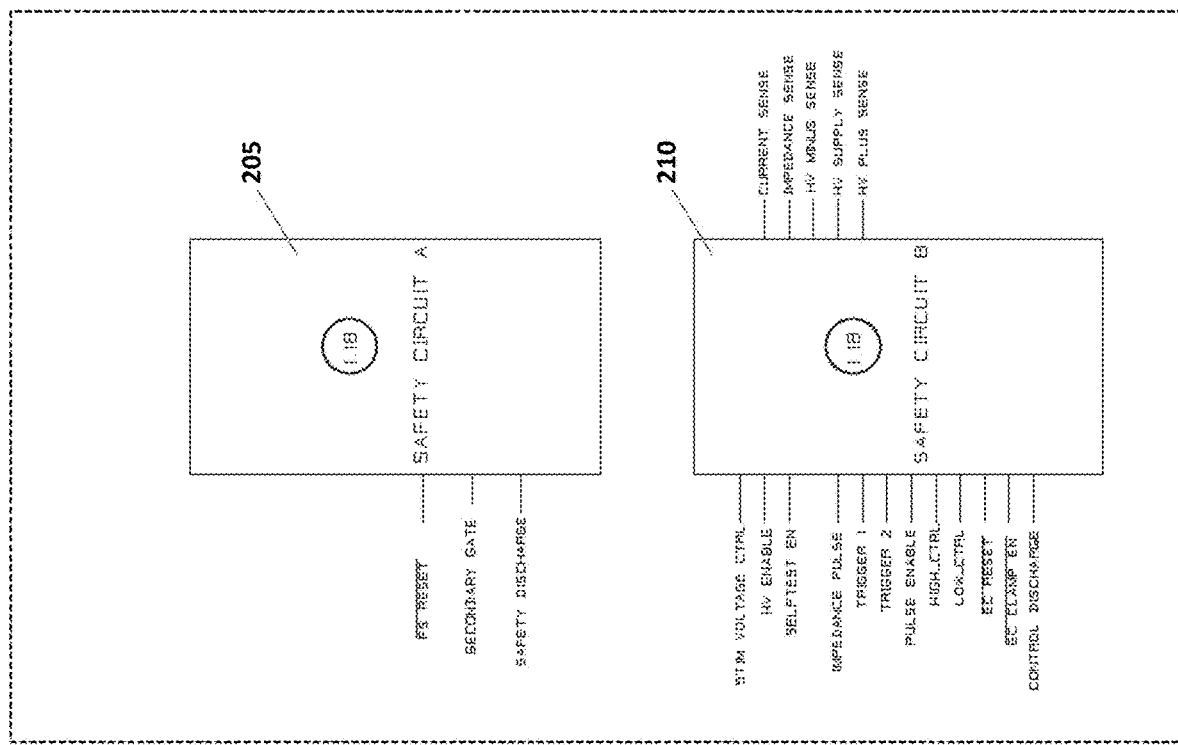
FIG. 2A is a block diagram illustration a first and second safety circuits of the stimulation module shown in FIG. 1B, in accordance with an embodiment of the present specification.

FIG. 2A is a block diagram illustration of first and second safety circuits of the stimulation module 120 of FIG. 1B, in accordance with an embodiment of the present specification. The first safety circuit element 205 comprises a microcontroller providing control signals to perform at least one of the following functions or tasks, but is not limited to said functions or tasks:

The safety circuit element 205 microcontroller includes a reset control signal that is an input to a current intensity digital-to-analog (DAC) converter. When the microcontroller asserts the control signal, the current intensity digital-to-analog (DAC) converter is held in reset. The current intensity digital-to-analog converter (DAC) of the stimulation module is held in reset by the microcontroller when the stimulation module is idle. The delivered current is proportional to the DAC voltage. Resetting the DAC sets the voltage to zero volts.

Figure 2B:
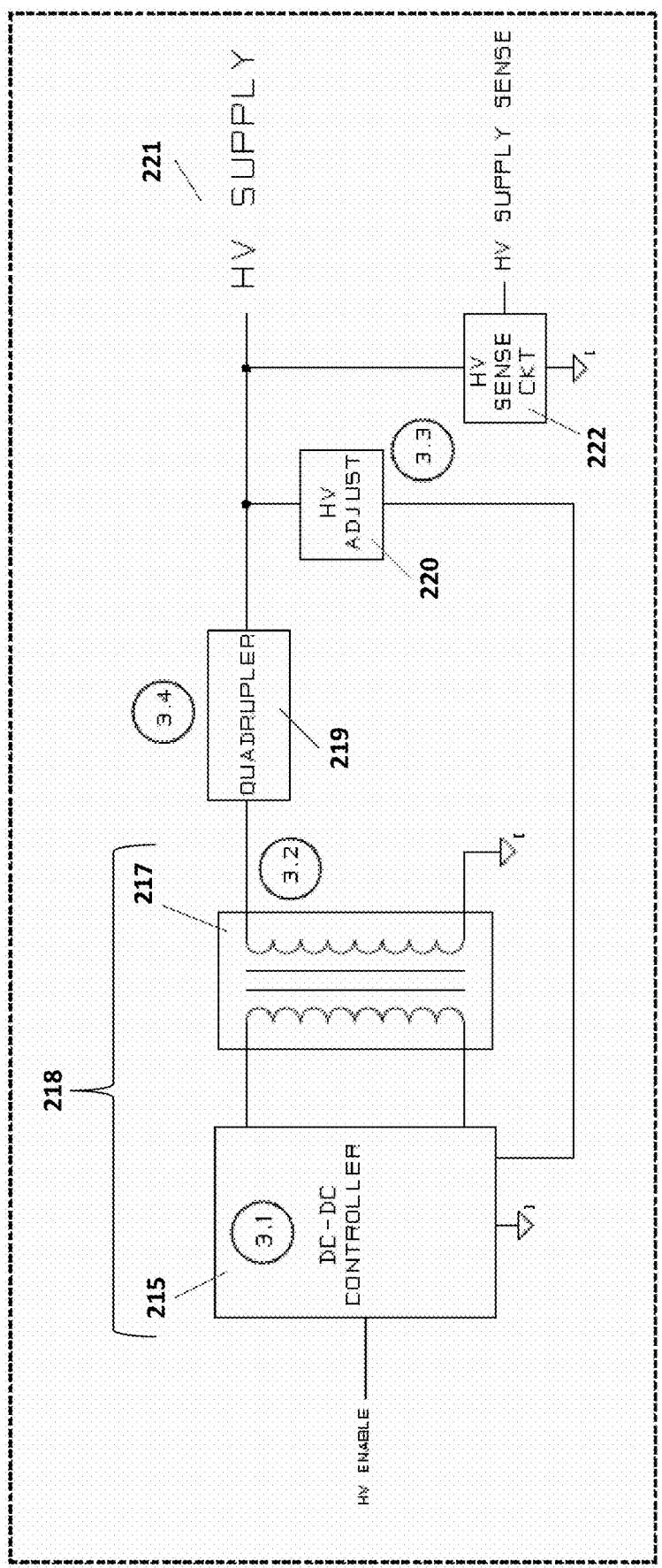
FIG. 2B is a block diagram illustrating a plurality of circuit elements for generating, adjusting and measuring supply voltage of the stimulation module of FIG. 1B, in accordance with an embodiment of the present specification.
Figure 2C:
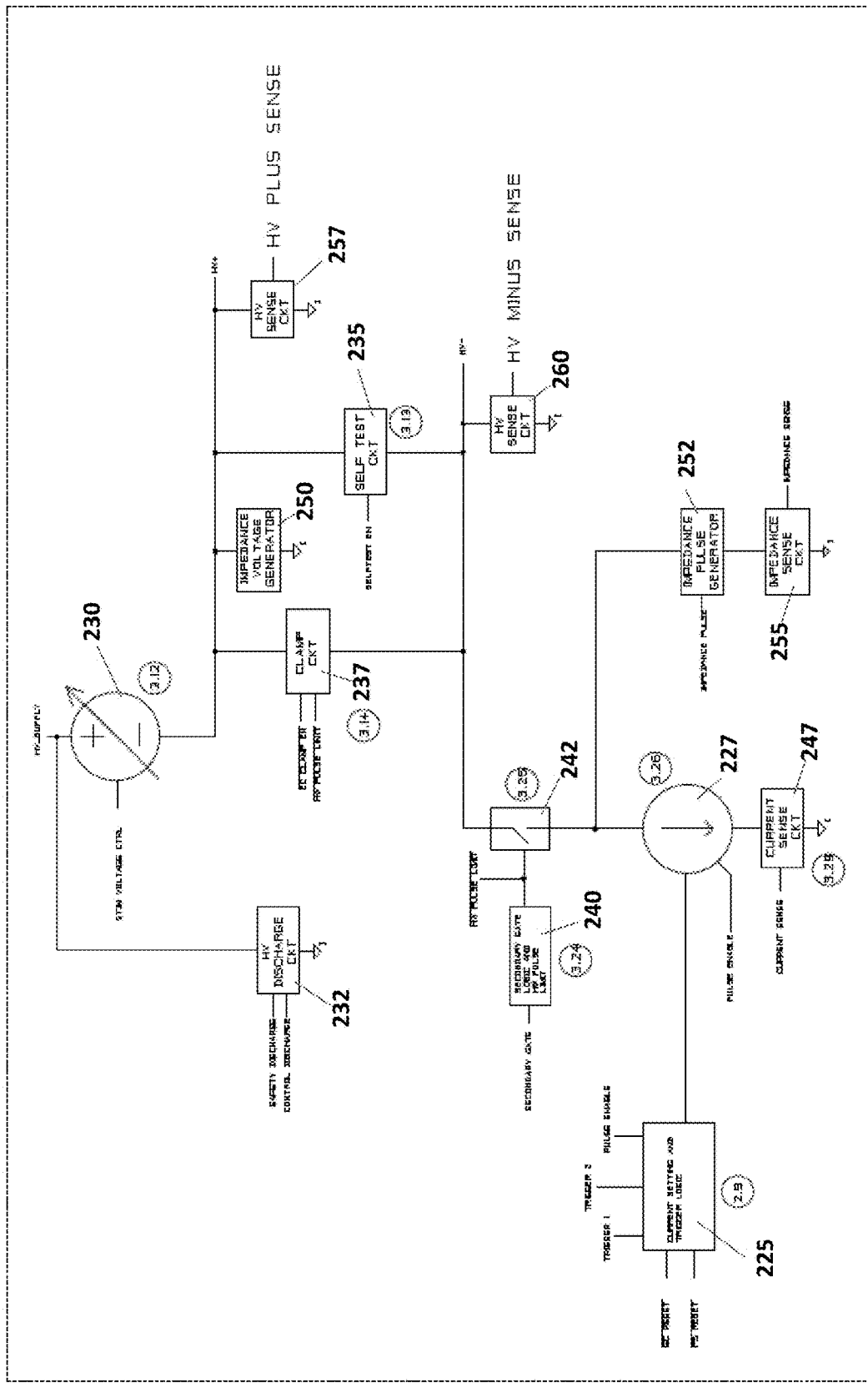
FIG. 2C is a block diagram illustrating a plurality of circuit elements for generating, adjusting and measuring output voltage and current, and for measuring electrode impedance of the stimulation module of FIG. 1B, in accordance with an embodiment of the present specification.

The safety circuit element 205 microcontroller further includes a pulse gate control signal that is an input to a current sink logic circuit element 240, as shown in FIG. 2C. The output of the current sink logic circuit element 240 enables or disables a current sink pulse gate 242. The current sink pulse gate 242 comprises an H-Bridge transformer driver, transformer, gate drive optocoupler, and a metal-oxide semiconductor field-effect transistor (MOSFET) acting as a switch. When the pulse gate control signal is asserted by the safety circuit element 205 microcontroller, the current sink logic element 240 activates the output of the gate drive optocoupler of the current sink pulse gate 242. This causes the gate drive optocoupler to switch an isolated DC voltage to the gate of the MOSFET transistor, causing it to conduct and allow the stimulation current sink to deliver current. The pulse gate control signal must be present at the same time a stimulus is fired to deliver the stimulation.

The safety circuit element 205 microcontroller further includes a discharge control signal for a 200 to 1200 volt supply circuit that is an input to a discharge circuit. The discharge circuit includes resistors, a negative-positive-negative (NPN) transistor, and a MOSFET transistor acting as a switch. When the safety circuit element 205 microcontroller asserts the control signal, the NPN transistor turns off. This causes a voltage to be applied to the gate of the MOSFET transistor via a pull-up resistor. The voltage at the gate of the MOSFET transistor causes the MOSFET transistor to conduct and discharge the 200 to 1200 volt supply storage capacitors of quadrupler circuit element 219, as shown in FIG. 2B, through current limiting series resistors to circuit ground.

The safety circuit element 205 microcontroller further includes a clamp control signal that is an input to a hardware clamp circuit 237, as shown in FIG. 2C. The hardware clamp circuit 237 consists of an optocoupler, a MOSFET transistor and resistors. When the safety circuit element 205 microcontroller asserts the clamp control signal, the optocoupler is disabled causing a voltage to be applied to the gate of the MOSFET transistor via pull-up resistors. The voltage at the gate of the MOSFET transistor causes the MOSFET transistor to conduct and short the positive (anode) and negative (cathode) stimulation nodes together. The hardware clamp circuit 237 is enabled when the stimulation module is idle. The hardware clamp circuit 237 ensures there is zero voltage potential between the positive (anode) and negative (cathode) nodes of the stimulation module.

The second safety circuit element 210 comprises a microcontroller providing control signals to perform at least one of the following functions or tasks, but is not limited to said functions or tasks:

The safety circuit element 210 microcontroller includes an internal digital-to-analog converter (DAC) that is connected to an input of a voltage source 230, as shown in FIG. 2C. The voltage source 230 consists of resistors, an operational amplifier and MOSFET transistors. The digital-to-analog converter generates a variable voltage between 0 and 3 volts. This voltage is connected to an input resistor network of the operational amplifier circuit in the voltage source 230. The resistor network provides DC bias and gain. The output of the operational amplifier circuit drives the gate of a first MOSFET transistor. The drain of the first MOSFET transistor is connected to the gate of a second MOSFET transistor. The first MOSFET transistor is operated in a linear region to adjust the voltage at the gate of the second MOSFET transistor. The drain of the second MOSFET transistor is connected to a 200 to 1200 volt supply rail. The source of the second MOSFET transistor is connected to the positive (anode) node of the stimulation module. The second MOSFET also operates in the linear region to vary the voltage across its drain and source. The resulting positive (anode) node voltage is the difference between the 200 to 1200 volt supply rail and the voltage across the drain to source of the second MOSFET transistor. This voltage is proportional to the digital-to-analog (DAC) voltage generated by the safety circuit element 210 microcontroller.

The safety circuit element 210 microcontroller further includes a supply voltage control signal and safety circuitry to enable and disable the 200 to 1200 volt supply 221, as shown in FIG. 2B. The safety circuit includes resistors and a MOSFET transistor. When the safety circuit element 210 microcontroller is inactive, a voltage is applied to the gate of the MOSFET transistor via a pull-up resistor, causing the MOSFET transistor to conduct and setting a DC-DC controller 215 ENABLE pin input to circuit ground, thereby disabling the DC-DC controller 215. The safety circuit element 210 microcontroller enables the DC-DC controller 215 by asserting the control signal causing the MOSFET transistor to turn off When the MOSFET transistor is off, a voltage is applied to the DC-DC controller 215 ENABLE pin via a pull-up resistor. This voltage enables the DC-DC controller 215.

The safety circuit element 210 microcontroller further includes a self-test load control signal that is an input to a self-test load circuit 235, shown in FIG. 2C. The self-test load circuit 235 consists of an optocoupler, a MOSFET transistor and resistors. When the safety circuit element 210 microcontroller asserts the control signal, the optocoupler is disabled causing a voltage to be applied to the gate of a MOSFET transistor via pull-up resistors. The voltage at the gate of the MOSFET transistor causes the MOSFET transistor to conduct and connect a self-test load between the positive (anode) and negative (cathode) stimulation nodes. The self-test load circuit 235 is disabled when the stimulation module is idle.

The safety circuit element 210 microcontroller further includes a pulse enable control signal and two current intensity trigger control signals for a trigger logic circuit element 225 and current sink circuit 227, shown in FIG. 2C. The trigger logic circuit element 225 consists of a digital-to-analog converter (DAC), logic gates and analog switches. The safety circuit element 210 configures two outputs of the digital-to-analog converter (DAC) according to the desired current intensity. The outputs of the digital-to-analog converter are connected to analog switches. The analog switches are controlled by the two current intensity trigger control signals and the logic gates. The safety circuit element 210 can quickly enable and disable an analog switch connected to the outputs of the digital-to-analog converter (DAC) by asserting and de-asserting the current intensity trigger control signals. When a switch is enabled, the digital-to-analog converter (DAC) voltage is presented to the current sink circuit 227. Under control of the safety circuit element 210, different voltages can be switched to the current sink circuit 227 allowing the stimulation module to quickly deliver different current intensities for each phase of a stimulus pulse. The safety circuit element 210 pulse enable control signal is input to the shutdown pin of an operational amplifier. The operational amplifier drives the gate of a MOSFET transistor with a voltage proportional to the digital-to-analog converter (DAC) voltage presented by the trigger logic circuit element 225. The voltage at the gate of the MOSFET causes the MOSFET transistor to conduct and sink a current through a ground referenced transistor. This is the stimulation module delivered current. The safety circuit element 210 pulse enable control signal must be asserted in order for the output pulse to be delivered.

Figure 2D:
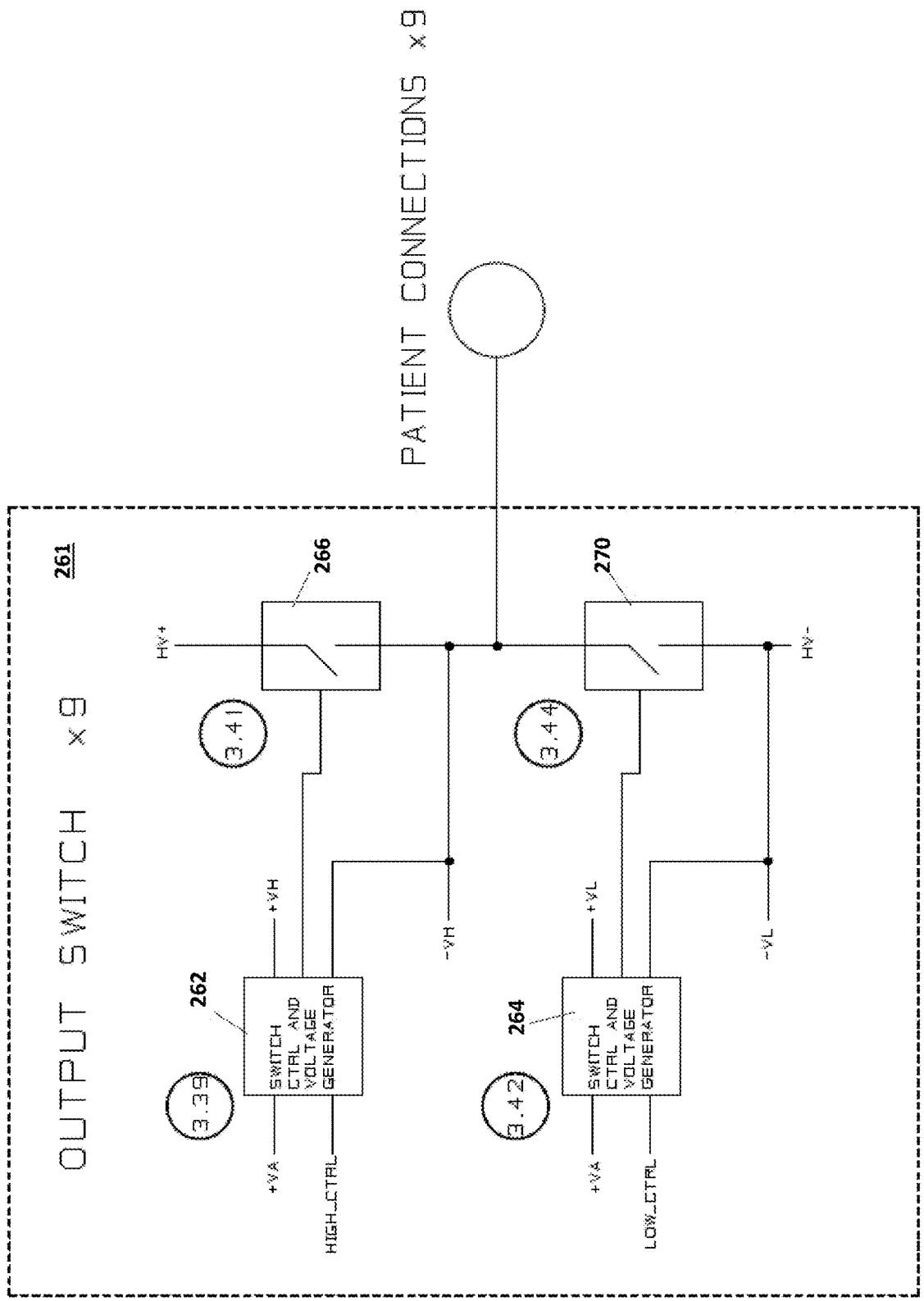
FIG. 2D is a block diagram illustration of an output switch of the stimulation module shown in FIG. 1B, in accordance with an embodiment of the present specification.

The safety circuit element 210 microcontroller further includes high- and low-side control signals for a patient connection circuit 261, shown in FIG. 2D. The patient connection circuit 261 consists of an H-Bridge transformer driver, transformers, gate drive optocouplers, and MOSFET transistors acting as switches. When the high-side patient connection control signal is asserted by the safety circuit element 210 microcontroller, the output of a gate drive optocoupler is activated. This causes the gate drive optocoupler to switch an isolated DC voltage to the gate of a high-side MOSFET transistor, causing it to conduct and connect the positive (anode) node to an output port 160. When the low-side patient connection control signal is asserted by the safety circuit element 210 microcontroller, the output of a gate drive optocoupler is activated. This causes the gate drive optocoupler to switch an isolated DC voltage to the gate of a low-side MOSFET transistor, causing it to conduct and connect the negative (cathode) node to an output port 160.

The safety circuit element 210 microcontroller further includes a reset control signal that is an input to the current intensity digital-to-analog (DAC) converter. When the microcontroller asserts the control signal, the current intensity digital-to-analog (DAC) converter is held in reset. The current intensity digital-to-analog converter (DAC) of the stimulation module is held in reset by the microcontroller when the stimulation module is idle. The delivered current is proportional to the DAC voltage. Resetting the DAC sets the voltage to zero volts.

The safety circuit element 210 microcontroller further includes a clamp control signal that is an input to the hardware clamp circuit 237. The hardware clamp circuit 237 consists of an optocoupler, a MOSFET transistor and resistors. When the safety circuit element 210 microcontroller asserts the control signal, the optocoupler is disabled causing a voltage to be applied to the gate of a MOSFET transistor via pull-up resistors. The voltage at the gate of the MOSFET transistor causes the MOSFET transistor to conduct and short the positive (anode) and negative (cathode) stimulation nodes together. The hardware clamp circuit 237 is enabled when the stimulation module is idle. The hardware clamp circuit 237 ensures there is zero voltage potential between the positive (anode) and negative (cathode) nodes of the stimulation module.

The safety circuit element 210 microcontroller further includes a discharge control signal for the 200 to 1200 volt supply circuit that is an input to the discharge circuit. The discharge circuit includes resistors, an NPN transistor, and a MOSFET transistor acting as a switch. When the safety circuit element 210 microcontroller asserts the control signal, the NPN transistor turns off. This causes a voltage to be applied to the gate of a MOSFET transistor via a pull-up resistor. The voltage at the gate of the MOSFET transistor causes the MOSFET transistor to conduct and discharge the 200 to 1200 volt supply storage capacitors of quadrupler circuit element 219 through current limiting series resistors to circuit ground.

Safety circuit element 210 microcontroller further includes internal analog-to-digital converter channels. These channels combined with voltage dividers or current sense resistors and operational amplifier buffers are used to sense the stimulation parameters such as, but not limited to, the delivered current, output voltage, supply voltage, impedance current.

The redundant safety circuits 205, 210 prevent unintended stimulation. Both circuits 205, 210 must be online and configured by the host computer (computing device 105 of FIG. 1A) to allow an output pulse to be delivered. If communication is lost between the stimulation module and the host computer, the stimulation module is powered down. Additionally, a 200 to 1200 volt power supply is designed to limit the available charge for the stimulus. The stimulation module limits the current in constant-voltage mode and limits the voltage in constant-current mode thereby preventing excessive energy from being delivered by the stimulation module when electrode impedance is very low or very high.

FIG. 2B is a block diagram illustration of a plurality of circuit elements for generating, adjusting and measuring supply voltage of the stimulation module 120 of FIG. 1B, in accordance with an embodiment of the present specification. Circuit element 215 is a DC-DC controller. In some embodiments, the DC-DC controller 215 is a flyback controller. Circuit element 217 is a transformer. In some embodiments, the transformer 217 is a flyback transformer. Circuit element 219 is a voltage quadrupler. Circuit elements 215 and 217 comprise a DC-DC flyback converter 218. The DC-DC flyback controller 215 generates a voltage on the secondary side of the transformer 217. This voltage is quadrupled through quadrupler circuit element 219 which contains a series of diodes and storage capacitors to generate a 200 to 1200 volt supply for the stimulation module. The DC-DC flyback controller 215, flyback transformer 217, and quadrupler circuit element 219 are a source of the delivered output voltage and current. Feedback loop circuit element 220 is connected between the output of the voltage quadrupler circuit element 219 and the feedback input on the DC-DC flyback controller 215.

Circuit element 220 consists of a digital-to-analog converter, operational amplifier, resistors and a MOSFET transistor. The digital-to-analog voltage and operational amplifier control the voltage applied to the gate of the MOSFET transistor to operate the MOSFET transistor in its linear region. Varying the digital-to-analog voltage varies the current through the MOSFET transistor and a resistor divider causing a voltage increase or decrease at the feedback node of the DC-DC flyback controller 215. When the feedback voltage is increased above a certain threshold, the DC-DC flyback controller 215 will reduce its duty cycle causing the voltage at the output of the DC-DC flyback converter 218 to decrease until the feedback voltage is within the threshold range. When the feedback voltage is decreased below a certain threshold, the DC-DC flyback controller 215 will increase its duty cycle causing the voltage at the output of the DC-DC flyback converter 218 to increase until the feedback voltage is within the threshold range. This behavior allows the output of the 200 to 1200 volt supply to be adjusted depending on the stimulation parameters. In various embodiments, the adjustable 200 to 1200 volt DC-DC converter 218 uses a digital-to-analog converter to vary the voltage in the feedback loop of the DC-DC flyback converter 218. This causes the DC-DC flyback controller 215 to adjust the switching duty cycle to raise or lower the output voltage. The adjustable nature of the circuit allows for built-in headroom which keeps the output voltage constant while the supply voltage decreases with each pulse. The 200 to 1200 volt supply can be turned off when not in use, reducing power consumption which allows for a battery-powered option. The high voltage sense circuit 222 provides a means of measuring the output voltage of the 200 to 1200 volt supply. High voltage sense circuit 222 consists of resistors, an operational amplifier and analog-to-digital converter. The output voltage of the 200 to 1200 volt supply is measured by dividing the voltage using a resistor divider, buffering the divided voltage and monitoring the buffered voltage with an internal analog-to-digital converter channel of circuit element 210 of FIG. 2A.

FIG. 2C is a block diagram illustration of a plurality of circuit elements for generating, adjusting and measuring output voltage and current, and for measuring electrode impedance of the stimulation module 120 of FIG. 1B, in accordance with an embodiment of the present specification. Trigger logic circuit element 225 comprises current intensity digital-to-analog converter (DAC) and intensity trigger logic of the stimulation module. The current intensity DAC generates voltage for a current sink circuit 227 that is proportional to a requested stimulus current intensity. The trigger logic allows the stimulation module to switch quickly between different current intensities.

Element 230 is a voltage source for setting an output voltage intensity. The 200 to 1200 volt supply discharge circuit 232 discharges the 200 to 1200 volt supply under the control of the safety circuit elements 205 and 210 of FIG. 2A. The 200 to 1200 volt supply discharge circuit includes resistors, an NPN transistor, and a MOSFET transistor acting as a switch. When safety circuit elements 205 or 210 assert a control signal, the NPN transistor turns off. This causes a voltage to be applied to the gate of a MOSFET transistor via a pull-up resistor. The voltage at the gate of the MOSFET transistor causes the MOSFET transistor to conduct and discharge the 200 to 1200 volt supply storage capacitors of quadrupler circuit element 219 through current limiting series resistors to circuit ground. Self-test load circuit 235 is used to test the stimulation module internally to ensure the stimulation module is working as expected.

Hardware clamp circuit 237 is activated under the control of the safety circuit elements 205 and 210 of FIG. 2A. When activated, the hardware clamp circuit 237 keeps the positive (anode) and negative (cathode) nodes of the stimulation module at the same potential. Element 240 is a current sink logic circuit that ensures that a stimulation pulse will terminate if a predefined pulse limit is exceeded.

A current sink pulse gate 242 is controlled by the safety circuit element 205 of FIG. 2A. The current sink pulse gate consists of an H-Bridge transformer driver, transformer, gate drive optocoupler, and a MOSFET transistor acting as a switch. When the pulse gate control signal is asserted by the safety circuit element 205 microcontroller, the output of the gate drive optocoupler is activated. This causes the gate drive optocoupler to switch the isolated DC voltage to the gate of the MOSFET transistor, causing it to conduct and allow the stimulation current sink to deliver current. This pulse gate must be asserted by the safety circuit element 205 at the same time the safety circuit element 210 attempts to fire a stimulus pulse or the pulse will not be delivered. The current setting and trigger logic circuit element 225 enables setting an output current intensity. Element 247 consists of a current sense resistor and operational amplifier buffer. The voltage across the current sense resistor is an input to the operational amplifier buffer. The output of the operational amplifier buffer is an input to a safety circuit element 210 microcontroller analog-to-digital converter channel. Element 247 provides a means of measuring the delivered current. The delivered current is monitored by the safety circuit element 210.

Impedance voltage generator 250 is a constant voltage source used in conjunction with an impedance pulse generator 252 and an impedance sense circuit 255 for measuring electrode impedance. A method of impedance calculation uses both successive approximation and averaging of 9 pulses, where each pulse is a combination of one output channel or port configured as an anode and the remaining channels configured as cathodes.

High voltage plus sense 257 and high voltage minus sense 260 provide means of measuring the delivered voltage. The delivered voltage is monitored by the safety circuit element 210. The voltage source 230 generates the output voltage for the stimulation module using an emitter follower field-effect transistor whose gate voltage is set by a digital-to-analog converter. The output voltage is proportional to the digital-to-analog converter voltage. A precision current sink is controlled by the trigger logic circuit element 225 that consists of two independent digital-to-analog converters and a high speed operational amplifier to control separate phases of a polyphasic pulse. The output current for the stimulation module is set by the digital-to-analog converter voltage at the input of the high speed operational amplifier which then forces the voltage across a ground referenced transistor at the output. The impedance pulse generator 252 and impedance sense circuit 255, consisting of a field-effect transistor, fixed impedance and an amplifier, are used to limit and sense the impedance current.

FIG. 2D is a block diagram illustration of a patient connection circuit, or output switch or port 261 of the stimulation module 120 of FIG. 1B, in accordance with an embodiment of the present specification. Circuit elements 262 and 264 generate voltage and control signals to connect and disconnect the patient connection circuit or output switch 261. Element 266 is a high-side (anode) patient switch while element 270 is a low-side (cathode) patient switch. In embodiments, there are nine output switches or ports, each similar to the patient connection circuit or output switch 261, forming the nine ports of the stimulation module 120. In embodiments, the nine output switches or ports are controlled by a gate drive optocoupler and H-Bridge transformer driver. This simplifies the high side switching circuit because there is no need for a charge pump to drive the high side output switch. Any combination of switches can be enabled simultaneously and all output switches can be set as anode or cathode.

In embodiments, current and voltage sensing are implemented using voltage dividers, amplifiers and analog-to-digital converters. Both sides of a high voltage rail are monitored along with the current to provide an accurate measurement of the delivered pulse. These values can also be used to compute an "on the fly" impedance measurement.

In embodiments, time clock synchronization of the stimulation module and one or more facilitation stimulators is accomplished with a precise digital timing signal and coordination of the timestamp by the host software (computing device 105 of FIG. 1A). This allows all stimulators and data acquisition and recording electrodes to be synchronized to each other within tens of microseconds.

Stimulation Parameters, Protocols or Schedules

The IONM software application of the present specification implements a plurality of stimulation protocols or schedules, comprising a plurality of stimulation parameters, that are available to the user for modulation, control and automatic delivery or application to a patient depending at least upon a neurostimulation and neuromonitoring objective such as, but not limited to, transcranial stimulation, cortical stimulation or direct nerve stimulation and/or a surgical procedure being performed. It should be appreciated that the IONM software application provides the user with a degree of ease, accuracy and automation with respect to delivery of intended stimuli and recordation of the stimuli as well as that of the correspondingly elicited neuromusculature response.

In various embodiments, stimulation protocols or schedules comprise driving a plurality of stimulation parameters such as, but not limited to, duration of the stimulation; time or moment of application of the stimulation sessions; intensity of stimulations, stimulation pulse shape, frequency, width, amplitude and polarity; stimulation duty cycle; stimulation continuity profile. Following are exemplary standard setting ranges for some of the stimulation parameters:

Pulse Width: 50 μsec to 500 μsec, and any increment therein

Pulse Amplitude: 0 A to 1.5 A, and any increment therein

Pulse Frequency: up to 1 Hz, and any increment therein

Pulse Shape: Monophasic positive, Monophasic negative, Biphasic, Polyphasic

Pulse Voltage: 0V to 1000V, and any increment therein

Mode of Stimulation: Single pulse stimulation, multi-pulse train (MPT) stimulation (comprising, for example, 3 to 5 pulses), Repetitive train stimulation Stimulation Method: Constant-voltage, Constant-current Inter-stimulus interval: 1 millisecond to 9.9 milliseconds (ms) and any increment therein Output Ports or Channels: each independently selectable as anode or cathode In various embodiments, the IONM software application implements a plurality of sub-sets of the aforementioned stimulation parameters and protocols depending at least upon the type of neurostimulation being delivered—such as, but not limited to, transcranial stimulation.

In some embodiments, the stimulation module 120 of FIG. 1B delivers polyphasic, double pulse or paired pulse train stimulation. In a paired pulse train, a first stimulus of each pair is referred to as the "conditioning or priming stimulus" and a second stimulus is referred to as the "test stimulus". The double pulse or paired pulse train stimulation improves signal acquisition by priming the nervous system with the first stimulus followed by the second stimulus (test stimulus). In some embodiments, the stimulation module 120 is in time synchronization with one or a plurality of facilitation stimulators. In accordance with an aspect of the present specification, the priming stimulus and the test stimulus are either from a single polyphasic pulse or from at least one facilitation stimulator in sync with the stimulation module 120.

In some embodiments, the stimulation module 120 is configured to deliver a lower intensity, longer pulse width stimulus, for example 200V and 500 uS, which reduces the threshold needed to elicit a neurological response. In embodiments, the stimulation module 120 can be operated for constant-current or constant-voltage output which provides a benefit of delivering an intended stimulus regardless of electrode impedance. In embodiments, the stimulation module 120 includes electrode impedance measurement and reports delivered current and voltage allowing the user to select an optimal stimulation method (that is, constant-current or constant-voltage) and determine if the stimulation module is delivering the intended stimulus.

Exemplary Use Cases

In accordance with various aspects of the present specification, the IONM system of the present specification enables the user to apply a plurality of stimulation protocols, patterns or schedules to the patient with none and/or minimal physical or electromechanical intervention, monitoring and management from the user. The IONM system of the present specification has application in a plurality of neurostimulation and neuromonitoring scenarios such as, but not limited to, transcranial stimulation whereby the motor cortex is stimulated using one or more stimulation probes/electrodes to determine functionality of the cortical structure (s), determine proximity to nervous system structures and create stimulation fields of varying size/depth.

The use case process flowcharts, being described henceforth, illustrate neurophysiological electrical stimulation treatment scenarios utilizing configurable and time-synchronized stimulators to elicit the best neurological response with minimal intervention required by a user. In the illustrated use case scenarios, it is assumed that the user has connected at least six of the nine outputs, of the stimulation module 120 of FIG. 1B, to a patient to allow for programmability of the stimulation parameters without the need for moving electrode connections to achieve a desired neurological response. Additionally, one to four independent electrical stimulators (henceforth, also referred to as 'facilitation stimulators') may be connected to the extremities of the patient for facilitation stimulation. In various embodiments, the facilitation stimulators may comprise stimulators such as, but not limited to, low-current electrical stimulator, direct cortical stimulator, constant-current electrical stimulator, constant-voltage electrical stimulator, audio evoked potential stimulator, and visual evoked potential stimulator.

The use case process flowcharts, being described henceforth, illustrate a plurality of functional features of the IONM system of the present specification in general and of the stimulation module 120 of FIG. 1B in particular. A non-limiting exemplary set, from the plurality of functional features, comprises: increasing the area of stimulation to improve a desired response and/or stimulate upper and lower extremities of the patient by adding additional anode sites to the montage, changing the stimulation mode from constant voltage to constant current to overcome issues due to electrode impedance, utilizing biphasic stimulation to elicit responses from both sides of the body with one stimulus, and facilitation stimulation to achieve a desired response at lower stimulation intensities.

Exemplary Use Case 1

Figure 3:
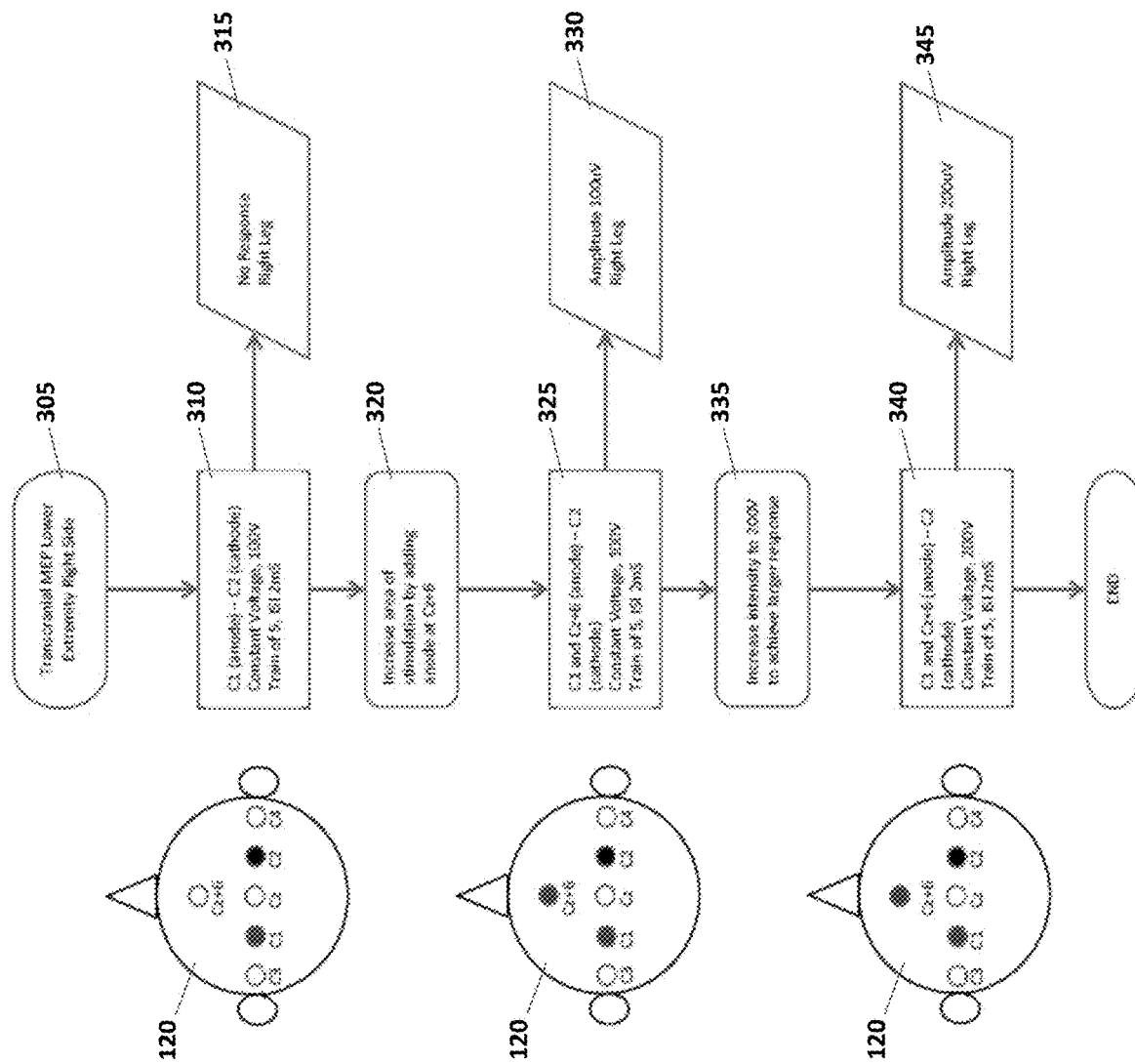
FIG. 3 is a flowchart describing a plurality of steps of a first use case of the IONM system of the present specification, illustrating transcranial stimulation and motor evoked potential (MEP) monitoring.

FIG. 3 is a flowchart illustrating a plurality of steps of a first use case of transcranial stimulation and motor evoked potential (MEP) monitoring, using the IONM system of the present specification. Also shown is the stimulation module 120 of FIG. 1B illustrating exemplary use of six of the nine output ports 160a-160i. The six output ports or channels are identified in FIG. 3 as $C_1$, $C_2$, $C_3$, $C_4$, $C_z$ and $C_{z+6}$.

Referring now to FIGS. 1A, 1B and 3, at step 305, a patient setup is established for transcranial stimulation and MEP recording or monitoring at a right side lower extremity, that is the right leg, of the patient. In an embodiment, MEP recording or sensing electrodes are positioned at muscle sites on the patient's right leg. Also, a plurality of stimulation components are connected to the six ports (of the stimulation module 120) and positioned at appropriate sites on the patient's head.

At step 310, the IONM software engine 105 activates ports $C_1$ (anode) and $C_2$ (cathode) of the stimulation module 120 to deliver stimulation. In an embodiment, the stimulation is delivered at a constant voltage of 100V using a train of 5 pulses having an inter-stimulus interval (ISI) of 2 ms. As a result of the delivered stimulation, no response is recorded at the patient's right leg at step 315. At step 320, the area of stimulation is increased by adding an anode at port $C_{z+6}$. At step 325, the IONM software engine 105 activates ports $C_1$ (anode), $C_{z+6}$ (anode) and $C_2$ (cathode) of the stimulation module 120 to deliver stimulation. The stimulation is delivered at a constant voltage of 100V using a train of 5 pulses having an inter-stimulus interval (ISI) of 2 ms. As a result of the delivered stimulation, a response of amplitude 100 µV is recorded at the patient's right leg at step 330. At step 335, the voltage intensity is increased to 200V to achieve a larger response at the patient's right leg. At step 340, the IONM software engine 105 activates ports $C_1$ (anode), $C_{z+6}$ (anode) and $C_2$ (cathode) of the stimulation module 120 to deliver stimulation. This time, the stimulation is delivered at an increased constant voltage of 200V using a train of 5 pulses having an inter-stimulus interval (ISI) of 2 ms. As a result of the delivered stimulation, a response of amplitude 200 µV is recorded at the patient's right leg at step 345.

Exemplary Use Case 2

Figure 4:
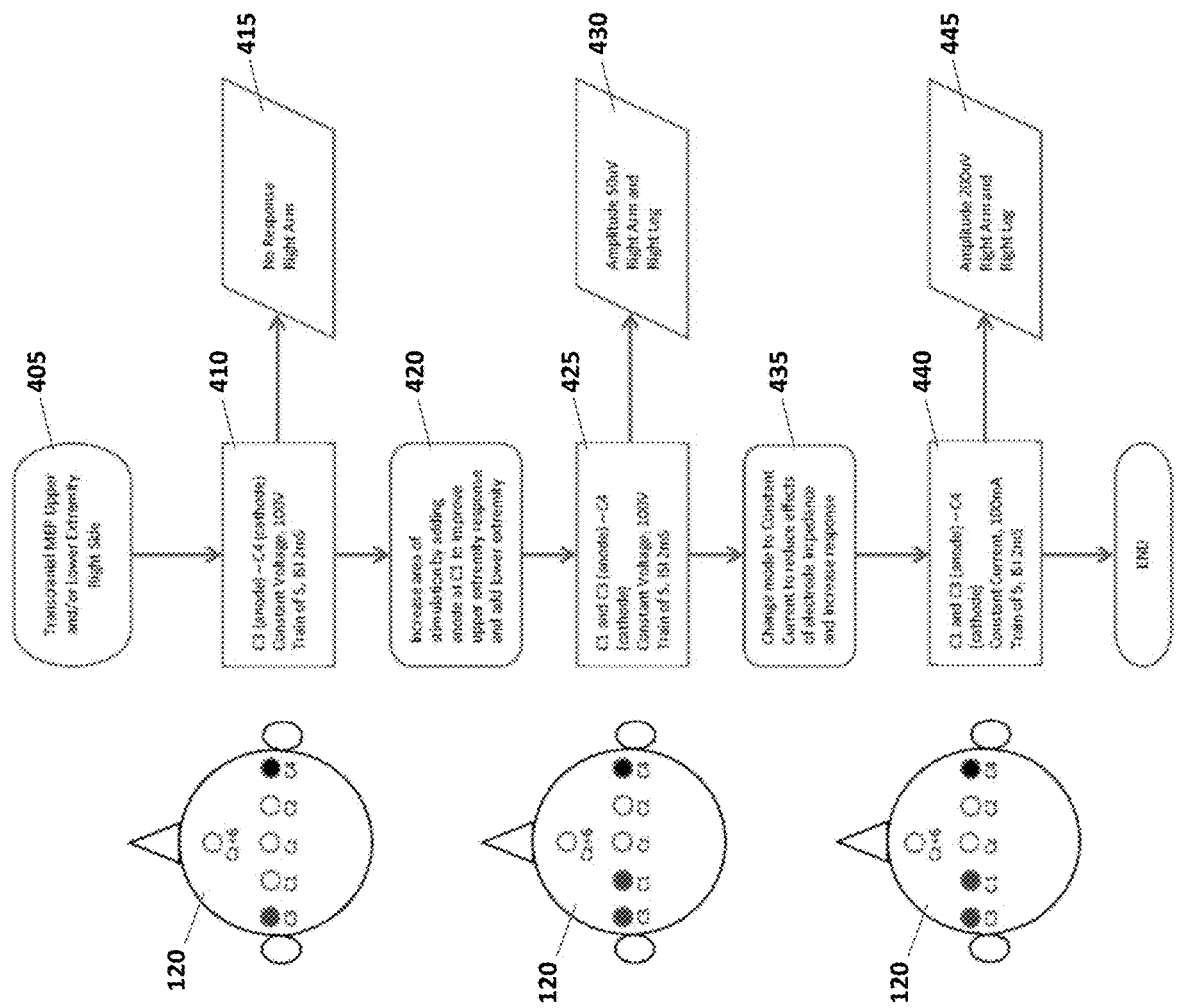
FIG. 4 is a flowchart describing a plurality of steps of a second use case of the IONM system of the present specification, illustrating transcranial stimulation and motor evoked potential (MEP) monitoring.

FIG. 4 is a flowchart illustrating a plurality of steps of a second use case of transcranial stimulation and motor evoked potential (MEP) monitoring, using the IONM system of the present specification. Also shown is the stimulation module 120 of FIG. 1B illustrating exemplary use of six of the nine output ports 160a-160i. The six output ports or channels are identified in FIG. 4 as $C_1$, $C_2$, $C_3$, $C_4$, $C_z$ and $C_{z+6}$.

Referring now to FIGS. 1A, 1B and 4, at step 405, a patient setup is established for transcranial stimulation and MEP recording or monitoring at right side upper and/or lower extremities, that is the right arm and right leg, of the patient. In an embodiment, MEP recording or sensing electrodes are positioned at muscle sites on the patient's right arm and right leg. Also, a plurality of stimulation components are connected to the six ports (of the stimulation module 120) and positioned at appropriate sites on the patient's head. At step 410, the IONM software engine 105 activates ports $C_3$ (anode) and $C_4$ (cathode) of the stimulation module 120 to deliver stimulation. In an embodiment, the stimulation is delivered at a constant voltage of 100V using a train of 5 pulses having an inter-stimulus interval (ISI) of 2 ms. As a result of the delivered stimulation, no response is recorded at the patient's right arm at step 415.

At step 420, the area of stimulation is increased by adding anode at port $C_1$ in order to improve response at the upper extremity (right arm) and elicit response at the lower extremity (right leg). At step 425, the IONM software engine 105 activates ports $C_1$ (anode), $C_3$ (anode) and $C_4$ (cathode) of the stimulation module 120 to deliver stimulation. The stimulation is delivered at a constant voltage of 100V using a train of 5 pulses having an inter-stimulus interval (ISI) of 2 ms. As a result of the delivered stimulation, a response of amplitude 50 μV is recorded at the patient's right arm and right leg, at step 430.

At step 435, the stimulation mode of the stimulation module 120 is changed from constant-voltage to constant-current to reduce effects of electrode impedance and increase response. At step 440, the IONM software engine 105 activates ports $C_1$ (anode), $C_3$ (anode) and $C_4$ (cathode) of the stimulation module 120 to deliver stimulation. This time, the stimulation is delivered at constant current of amplitude 100 mA, using a train of 5 pulses having an inter-stimulus interval (ISI) of 2 ms. As a result of the delivered stimulation, a response of amplitude 200 μV is recorded at the patient's right arm and right leg, at step 445.

Exemplary Use Case 3

Figure 5:
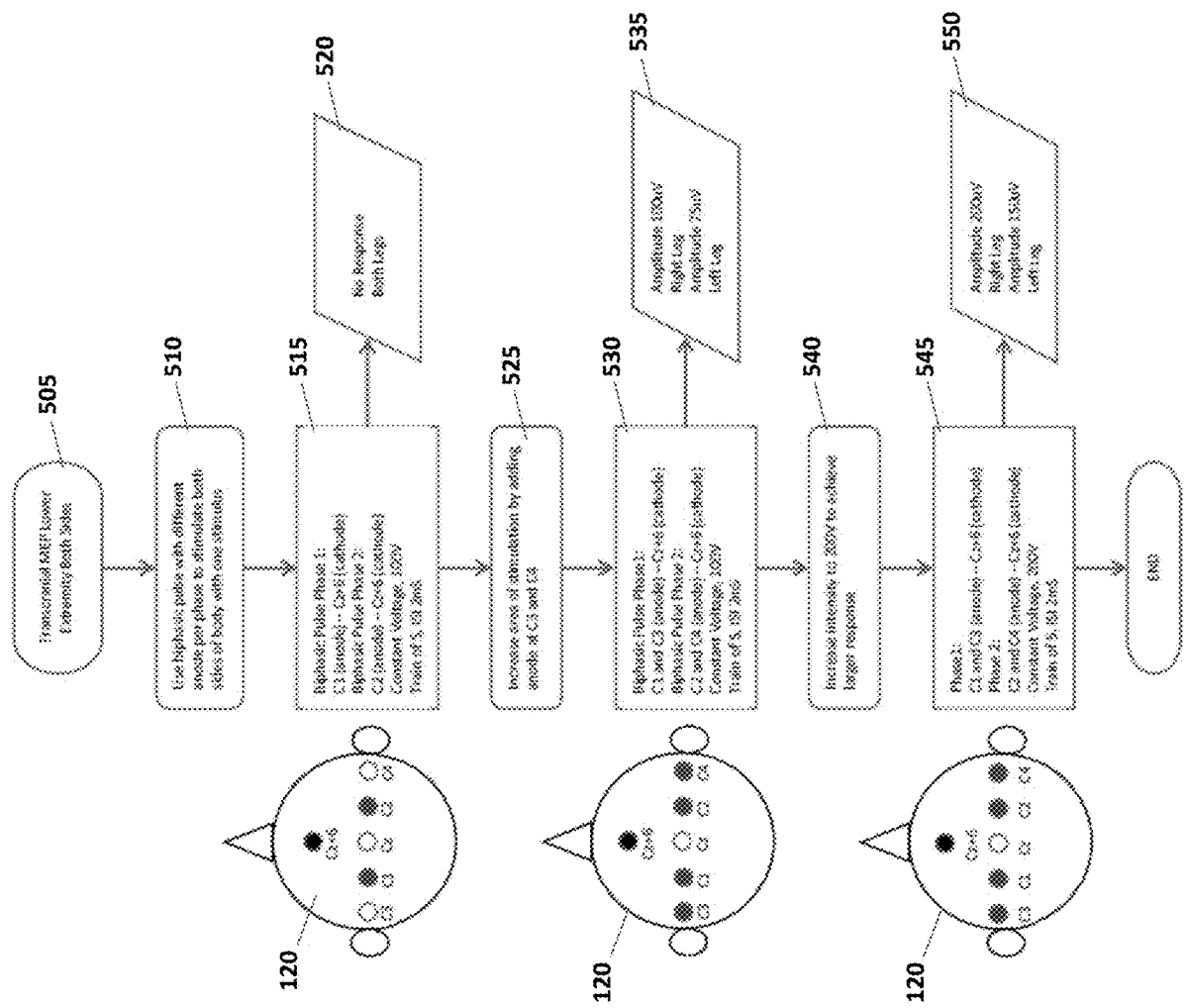
FIG. 5 is a flowchart describing a plurality of steps of a third use case of the IONM system of the present specification, illustrating transcranial stimulation and motor evoked potential (MEP) monitoring.

FIG. 5 is a flowchart illustrating a plurality of steps of a third use case of transcranial stimulation and motor evoked potential (MEP) monitoring, using the IONM system of the present specification. Also shown is the stimulation module 120 of FIG. 1B illustrating exemplary use of six of the nine output ports 160a-160i. The six output ports or channels are identified in FIG. 5 as $C_1$, $C_2$, $C_3$, $C_4$, $C_z$ and $C_{z+6}$.

Referring now to FIGS. 1A, 1B and 5, at step 505, a patient setup is established for transcranial stimulation and MEP recording or monitoring at lower extremities on both sides, that is the left and right legs, of the patient. In an embodiment, MEP recording or sensing electrodes are positioned at muscle sites on the patient's left and right legs. Also, a plurality of stimulation components are connected to the six ports (of the stimulation module) and positioned at appropriate sites on the patient's head. At step 510, a stimulation protocol is chosen or activated, at the IONM software engine 105, to use a biphasic pulse with a different anode per phase to stimulate both sides of the patient's body with one stimulus. At step 515, in order to deliver stimulation, the IONM software engine 105 activates ports $C_1$ (anode) and $C_{z+6}$ (cathode) of the stimulation module 120 during the first phase of the biphasic pulse and activates ports $C_2$ (anode) and $C_{z+6}$ (cathode) of the stimulation module 120 during the second phase of the biphasic pulse. In an embodiment, the stimulation is delivered at a constant voltage of 100V using a train of 5 pulses having an inter-stimulus interval (ISI) of 2 ms. As a result of the delivered stimulation, no response is recorded at any of the patient's legs at step 520.

At step 525, the area of stimulation is increased by adding anode at ports $C_3$ and $C_4$. At step 530, in order to deliver stimulation, the IONM software engine 105 activates ports $C_1$ (anode), $C_3$ (anode) and $C_{z+6}$ (cathode) of the stimulation module 120 during the first phase of the biphasic pulse and activates ports $C_2$ (anode), $C_4$ (anode) and $C_{z+6}$ (cathode) of the stimulation module 120 during the second phase of the biphasic pulse. In an embodiment, the stimulation is delivered at a constant voltage of 100V using a train of 5 pulses having an inter-stimulus interval (ISI) of 2 ms. As a result of the delivered stimulation, a response of amplitude 100 μV is recorded at the patient's right leg and a response of amplitude 75 μV is recorded at the patient's left leg, at step 535.

Now, at step 540, the voltage intensity is increased to 200V to achieve larger response at the patient's left and right legs. At step 545, the IONM software engine 105 activates ports $C_1$ (anode), $C_3$ (anode) and $C_{z+6}$ (cathode) of the stimulation module 120 during the first phase of the biphasic pulse and activates ports $C_2$ (anode), $C_4$ (anode) and $C_{z+6}$ (cathode) of the stimulation module 120 during the second phase of the biphasic pulse. In an embodiment, the stimulation is delivered at an increased constant voltage of 200V using a train of 5 pulses having an inter-stimulus interval (ISI) of 2 ms. As a result of the delivered stimulation, a response of amplitude 200 μV is recorded at the patient's right leg and a response of amplitude 150 μV is recorded at the patient's left leg, at step 550.

Exemplary Use Case 4

Figure 6:
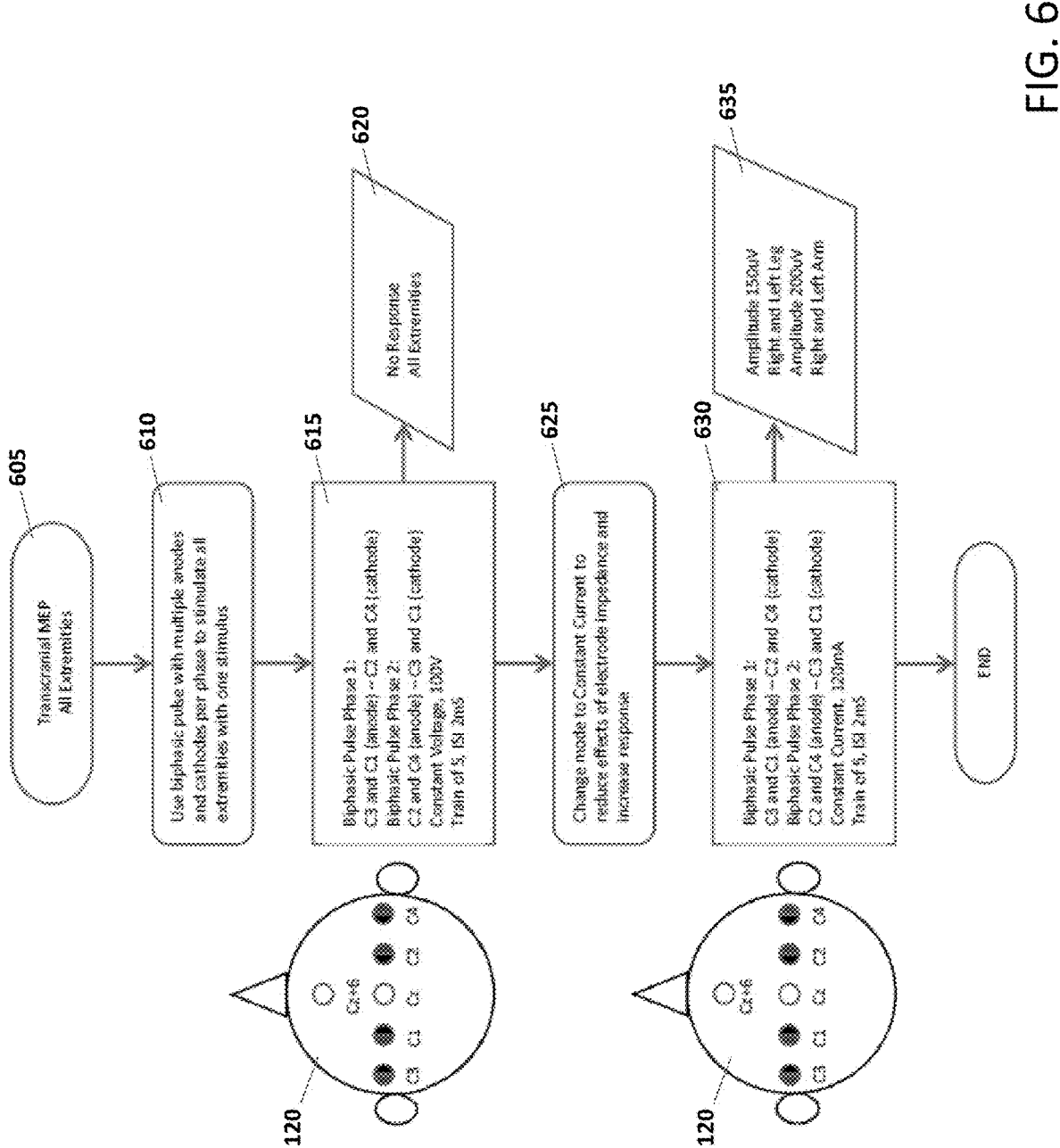
FIG. 6 is a flowchart describing a plurality of steps of a fourth use case of the IONM system of the present specification, illustrating transcranial stimulation and motor evoked potential (MEP) monitoring.

FIG. 6 is a flowchart illustrating a plurality of steps of a fourth use case of transcranial stimulation and motor evoked potential (MEP) monitoring, using the IONM system of the present specification. Also shown is the stimulation module 120 of FIG. 1B illustrating exemplary use of six of the nine output ports 160a-160i. The six output ports or channels are identified in FIG. 6 as $C_1$, $C_2$, $C_3$, $C_4$, $C_z$ and $C_{z+6}$.

Referring now to FIGS. 1A, 1B and 6, at step 605, a patient setup is established for transcranial stimulation and MEP recording or monitoring at all extremities, including the left and right arms as well as the left and right legs, of the patient. In an embodiment, MEP recording or sensing electrodes are positioned at muscle sites on the patient's left and right arms as well as left and right legs. Also, a plurality of stimulation components are connected to the six ports (of the stimulation module 120) and positioned at appropriate sites on the patient's head.

At step 610, a stimulation protocol is chosen or activated, at the IONM software engine 105, to use a biphasic pulse with multiple anodes and cathodes per phase to stimulate all extremities of the patient's body with one stimulus. At step 615, in order to deliver stimulation, the IONM software engine 105 activates ports $C_3$ (anode), $C_1$ (anode), $C_2$ (cathode) and $C_4$ (cathode) of the stimulation module 120 during the first phase of the biphasic pulse and activates ports $C_2$ (anode), $C_4$ (anode), $C_3$ (cathode) and $C_1$ (cathode) of the stimulation module 120 during the second phase of the biphasic pulse. In an embodiment, the stimulation is delivered at a constant voltage of 100V using a train of 5 pulses having an inter-stimulus interval (ISI) of 2 ms. As a result of the delivered stimulation, no response is recorded at any of the patient's extremities at step 620.

Now, at step 625, the mode of stimulation is modified from constant-voltage to constant-current to reduce effects of electrode impedance and increase response. At step 630, in order to deliver stimulation, the IONM software engine 105 activates ports $C_3$ (anode), $C_1$ (anode), $C_2$ (cathode) and $C_4$ (cathode) of the stimulation module 120 during the first phase of the biphasic pulse and activates ports $C_2$ (anode), $C_4$ (anode), $C_3$ (cathode) and $C_1$ (cathode) of the stimulation module 120 during the second phase of the biphasic pulse. In an embodiment, the stimulation is delivered at a constant current of amplitude 120 mA using a train of 5 pulses having an inter-stimulus interval (ISI) of 2 ms. As a result of the delivered stimulation, a response of amplitude 150 μV is recorded at the patient's left and right legs and a response of amplitude 200 μV is recorded at the patient's left and right arms, at step 635.

Exemplary Use Case 5

Figure 7:
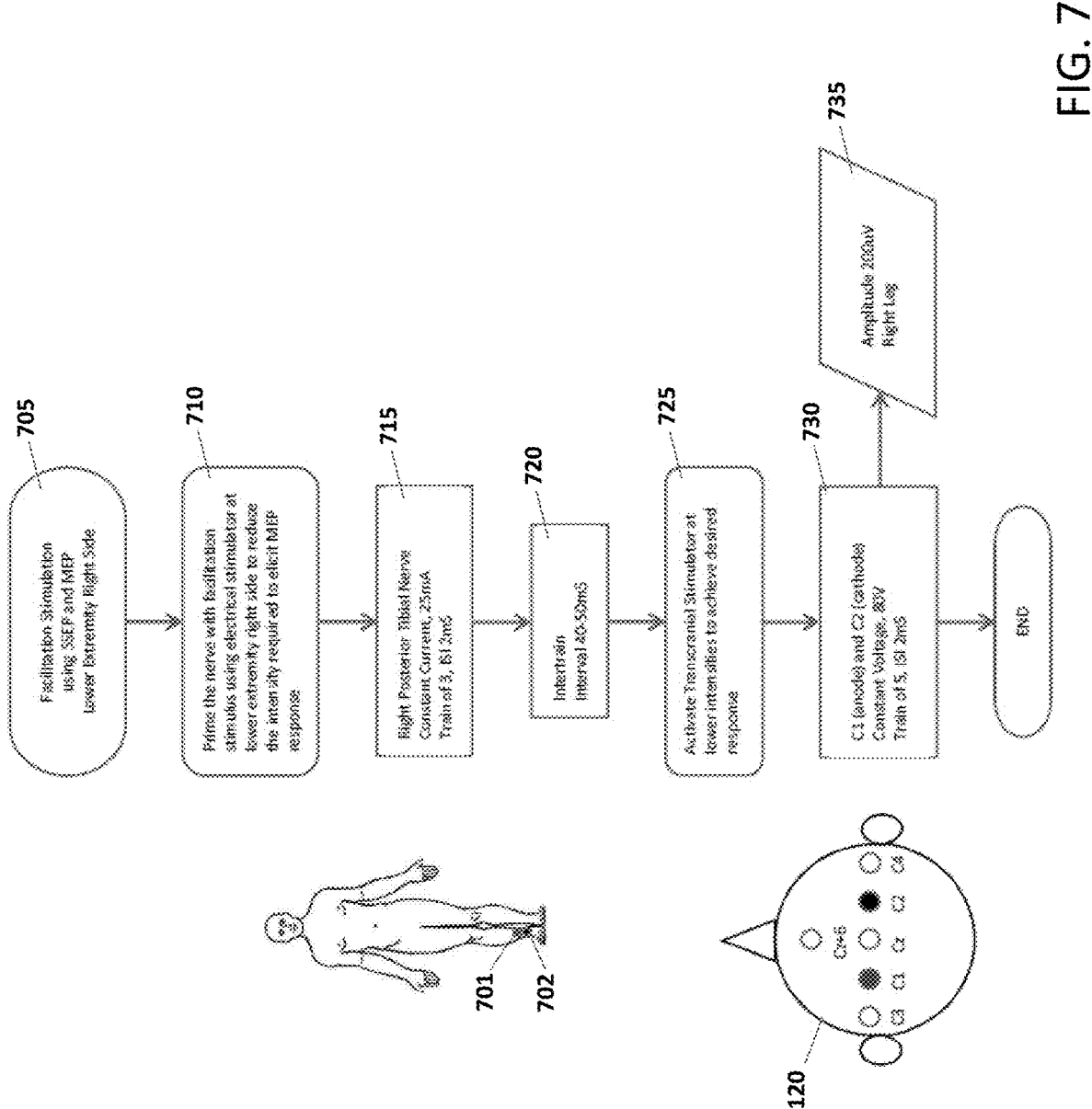
FIG. 7 is a flowchart illustrating a plurality of steps of a fifth use case of the IONM system of the present specification, illustrating the facilitation of stimulation.

FIG. 7 is a flowchart illustrating a plurality of steps of a fifth use case of facilitation stimulation, using the IONM system of the present specification. Also shown is the stimulation module 120 of FIG. 1B illustrating exemplary use of six of the nine output ports 160a-160i. The six output ports or channels are identified in FIG. 7 as $C_1$, $C_2$, $C_3$, $C_4$, $C_z$ and $C_{z+6}$.

Referring now to FIGS. 1A, 1B and 7, at step 705, a patient setup is established for transcranial stimulation using SSEP (Somatosensory Evoked Potential) stimulation and MEP (Motor Evoked Potential) recording or monitoring at lower extremity right side, that is the right leg, of a patient. In an embodiment, MEP recording or sensing electrodes are positioned at muscle sites on the patient's right leg. In accordance with an embodiment, facilitation stimulators 701 and 702 are also positioned at lower extremity right side, that is the right leg, of the patient. Also, a plurality of stimulation components are connected to the six ports (of the stimulation module 120) and positioned at appropriate sites on the patient's head. In accordance with an aspect, the IONM software engine 105 ensures that the stimulation module 120 and the facilitation stimulators 701 and 702 are in time-synchronization with each other.

At step 710, a stimulation protocol is chosen or activated, at the IONM software engine 105, to initiate a facilitation stimulus using the facilitation stimulators 701 and 702 positioned at the lower extremity right side to reduce an intensity of stimulation required (from the stimulation module 120) to elicit an MEP response. Now, at step 715, the IONM software engine 105 activates the facilitation stimulators 701 and 702 to deliver a facilitation stimulus to the patient's right posterior tibial nerve. In one embodiment, the facilitation stimulus is delivered at a constant current of amplitude 25 mA using a train of 3 pulses having an inter-stimulus interval (ISI) of 2 ms. At step 720, the inter-stimulus interval of the facilitation stimulus is modulated in a range of 40 ms to 50 ms.

Now, at step 725, the IONM software engine 105 configures the stimulation module 120 to deliver a stimulation protocol having relatively lower intensities to achieve desired responses. At step 730, in one embodiment, the IONM software engine 105 activates $C_1$ (anode) and $C_2$ (cathode) of the stimulation module 120 to deliver stimulation. In one embodiment, the stimulation is delivered at a constant voltage of amplitude 80V using a train of 5 pulses having an inter-stimulus interval (ISI) of 2 ms. As a result of the delivered stimulation, a response of amplitude 200 µV is recorded at the patient's right leg, at step 735.

Exemplary Use Case 6

Figure 8:
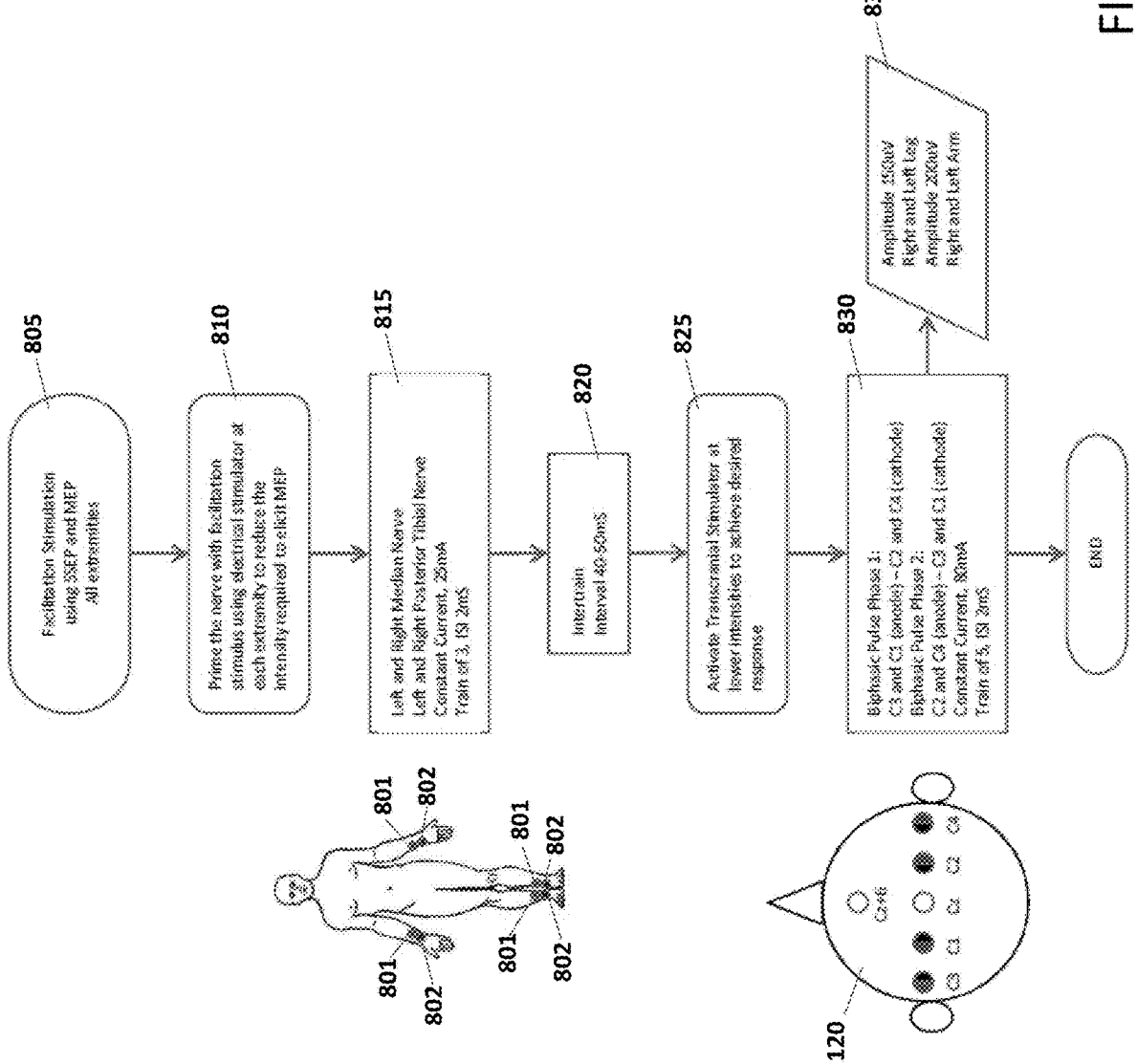
FIG. 8 is a flowchart illustrating a plurality of steps of a sixth use case of the IONM system of the present specification, illustrating the facilitation of stimulation.

FIG. 8 is a flowchart illustrating a plurality of steps of a sixth use case of facilitation stimulation, using the IONM system of the present specification. Also shown is the stimulation module 120 of FIG. 1B illustrating exemplary use of six of the nine output ports 160a-160i. The six output ports or channels are identified in FIG. 7 as $C_1$, $C_2$, $C_3$, $C_4$, $C_z$ and $C_{z+6}$.

Referring now to FIGS. 1A, 1B and 8, at step 805, a patient setup is established for transcranial stimulation using SSEP (Somatosensory Evoked Potential) stimulation and MEP (Motor Evoked Potential) recording or monitoring at all extremities, that is the left and right arms as well as the left and right legs, of a patient. In an embodiment, MEP recording or sensing electrodes are positioned at muscle sites on the patient's left and right arms as well as the left and right legs. In accordance with an embodiment, facilitation stimulators 801 and 802 are also positioned at the left and right arms as well as the left and right legs, of the patient. Also, a plurality of stimulation components are connected to the six ports (of the stimulation module 120) and positioned at appropriate sites on the patient's head. In accordance with an aspect, the IONM software engine 105 ensures that the stimulation module 120 and the facilitation stimulators 801 and 802 are in time-synchronization with each other.

At step 810, a stimulation protocol is chosen or activated, at the IONM software engine 105, to initiate a facilitation stimulus using the facilitation stimulators 801 and 802 positioned at all extremities reduce an intensity of stimulation required (from the stimulation module 120) to elicit an MEP response. Now, at step 815, the IONM software engine 105 activates the facilitation stimulators 801 and 802 to deliver facilitation stimulus at the patient's left and right median nerve as well as the left and right posterior tibial nerve. In one embodiment, the facilitation stimulus is delivered at a constant current of amplitude 25 mA using a train of 3 pulses having an inter-stimulus interval (ISI) of 2 ms. At step 820, the inter-stimulus interval of the facilitation stimulus is modulated in a range of 40 ms to 50 ms.

Now, at step 825, the IONM software engine 105 configures the stimulation module 120 to deliver a stimulation protocol having relatively lower intensities to achieve desired responses.

At step 830, in order to deliver stimulation, the IONM software engine 105 activates ports $C_3$ (anode), $C_1$ (anode), $C_2$ (cathode) and $C_4$ (cathode) of the stimulation module 120 during a first phase of a biphasic stimulation pulse and activates ports $C_2$ (anode), $C_4$ (anode), $C_3$ (cathode) and $C_1$ (cathode) of the stimulation module 120 during a second phase of the biphasic stimulation pulse. In an embodiment, the stimulation is delivered at a constant current of amplitude 80 mA using a train of 5 pulses having an inter-stimulus interval (ISI) of 2 ms. As a result of the delivered stimulation, a response of amplitude 150 µV is recorded at the patient's left and right legs while a response of amplitude 200 µV is recorded at the patient's left and right arms, at step 835.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A stimulation module configured to generate and deliver an electrical stimulus comprising at least two successive stimulation pulses, the stimulation module comprising:

a plurality of output ports adapted to connect to a plurality of stimulation electrodes;

a controller, wherein the controller is configured to simultaneously activate any combination of the plurality of output ports, is configured to designate a first portion of the plurality of output ports to being an anode and to designate a second portion of the plurality of output ports to being a cathode for a first of the at least two successive stimulation pulses, and, for a second of the at least two successive stimulation pulses, is configured to change a designation of a third portion of the plurality of output ports to being a cathode and to a designation of a fourth portion of the plurality of output ports to being an anode, wherein output ports in the third portion is different than output ports in the first portion and wherein output ports in the fourth portion is different than output ports in the second portion;

a pulse generator in electrical communication with the controller, wherein the pulse generator comprises:

a constant current sink adapted to enable a setting of an intensity of an output current of the stimulation module;

a current intensity digital-to-analog converter adapted to generate voltage for the constant current sink that is proportional to the set output current intensity;

trigger logic adapted to enable the stimulation module to switch between a plurality of current intensities; and a current sense circuit configured to measure delivered current; and a constant voltage source adapted to enable a setting of an intensity of an output voltage of the stimulation module.

2. The stimulation module of claim 1, further comprising an impedance circuit comprising an impedance voltage generator, an impedance pulse generator, and an impedance sense circuit, wherein the impedance circuit is configured to measure impedance of the plurality of stimulation electrodes.

3. The stimulation module of claim 1, further comprising an adjustable voltage converter, wherein the adjustable voltage converter is configured to adjust a voltage to raise or lower the output supply voltage.

4. The stimulation module of claim 1, wherein the stimulation module is operably connected to a computing device of an intraoperative neurophysiological monitoring (IONM) system and wherein the controller comprises an IONM software engine adapted to execute in the computing device.

5. The stimulation module of claim 1, wherein the plurality of outputs ports comprises at least nine output ports.

6. The stimulation module of claim 1, further comprising an adjustable voltage converter, wherein the adjustable voltage converter is a DC to DC voltage converter and is configured to convert a voltage in a range of 200 to 1200 volts.

7. The stimulation module of claim 6, wherein the adjustable voltage converter comprises a digital-to-analog converter and wherein the digital-to-analog converter is configured to vary a voltage in a feedback loop of the DC-DC voltage converter thereby causing a DC-DC controller to adjust a switching duty cycle to raise or lower the output supply voltage.

8. The stimulation module of claim 1, wherein the constant voltage source generates an output voltage using a field-effect transistor.

9. The stimulation module of claim 8, wherein a gate voltage of the field-effect transistor is set by a digital-to-analog converter and wherein the output voltage is proportional to the digital-to-analog converter voltage.

10. The stimulation module of claim 1, wherein the constant current sink comprises two digital-to-analog converters and an amplifier configured to control separate phases of the at least two successive stimulation pulses.

11. The stimulation module of claim 1, wherein the output current is configured to be set by an adjustable voltage converter at an input of an amplifier.

12. The stimulation module of claim 11, wherein the setting of the output current is adapted to force a voltage across a ground referenced transistor.

13. The stimulation module of claim 1, wherein the pulse generator comprises a field-effect transistor and an amplifier, and wherein the pulse generator is adapted to limit and sense an impedance current.

14. The stimulation module of claim 1, wherein the plurality of output ports is configured to be controlled by a gate drive optocoupler and an H-Bridge transformer driver.

15. The stimulation module of claim 1, wherein the controller is configured to monitor voltage values on a first side and a second side of a voltage rail, wherein the controller is configured to monitor a value of current, and wherein the controller is configured to output a measurement of a delivered pulse based upon the monitored voltage values and the monitored current value.

16. The stimulation module of claim 15, wherein the controller is adapted to use the monitored voltage values and the monitored current value to compute an impedance value.

17. The stimulation module of claim 1, wherein the stimulation module is configured to be in time synchronization with a plurality of facilitation stimulators and a plurality of recording electrodes and wherein the plurality of facilitation stimulators and the plurality of recording electrodes are in data communication with a computing device of an intraoperative neurophysiological monitoring (IONM) system.

18. The stimulation module of claim 17, further comprising a digital timing signal and wherein the time synchronization is achieved using the digital timing signal and coordination of a timestamp by the computing device.

19. The stimulation module of claim 1, wherein one of the at least two successive stimulation pulses is polyphasic.

20. The stimulation module of claim 1, wherein the stimulation module is configured to generate the at least two successive stimulation pulses having a voltage in a range of 0 to 1000 Volts and a current in a range of 0 to 1.5 Amps in any combination of single pulses or pulse trains.

21. The stimulation module of claim 1, wherein the controller is configured to modulate at least one of a plurality of stimulation parameters of the at least two successive stimulation pulses.

22. The stimulation module of claim 1, further comprising an impedance circuit configured to measure an impedance of the plurality of stimulation electrodes based upon a plurality of pulses, wherein the plurality of pulses is generated by combination of one of the plurality of output ports being configured as an anode and remaining ones of the plurality of output ports being configured as cathodes.

23. The stimulation module of claim 1, wherein the stimulation module is configured to operate in a constant voltage mode and wherein the output current is limited in the constant voltage mode.

24. The stimulation module of claim 1, wherein the stimulation module is configured to operate in a constant current mode and wherein the output voltage is limited in the constant current mode.

25. The stimulation module of claim 1, further comprising first and second safety circuits.

26. The stimulation module of claim 1, wherein the stimulation module is configured to be powered down if communication is lost between the stimulation module and a computing device of an intraoperative neurophysiological monitoring (IONM) system.

* * * * *